US008680036B2

(12) United States Patent
Gonzales et al.

(10) Patent No.: US 8,680,036 B2
(45) Date of Patent: Mar. 25, 2014

(54) LIQUID CLEANING COMPOSITION COMPRISING COLOR-STABLE POLYURETHANE ABRASIVE PARTICLES

(75) Inventors: Denis Alfred Gonzales, Brussels (BE); Aicha Dkidak, Brussels (BE)

(73) Assignee: The Procter & Gamble Company, Cincinnati, OH (US)

( * ) Notice: Subject to any disclaimer, the term of this patent is extended or adjusted under 35 U.S.C. 154(b) by 1 day.

(21) Appl. No.: 12/972,603

(22) Filed: Dec. 20, 2010

(65) Prior Publication Data

US 2011/0150950 A1 Jun. 23, 2011

Related U.S. Application Data

(60) Provisional application No. 61/288,887, filed on Dec. 22, 2009, provisional application No. 61/326,286, filed on Apr. 21, 2010, provisional application No. 61/326,290, filed on Apr. 21, 2010.

(51) Int. Cl.
*C11D 3/14* (2006.01)

(52) U.S. Cl.
USPC ........... 510/395; 510/130; 510/139; 510/236; 510/268; 510/368; 510/438

(58) Field of Classification Search
USPC .......... 510/130, 139, 236, 268, 368, 395, 438
See application file for complete search history.

(56) References Cited

U.S. PATENT DOCUMENTS

| | | | |
|---|---|---|---|
| 1,621,906 A | 3/1927 | Schless | |
| 2,082,275 A | 6/1937 | Daimler et al. | |
| 2,084,632 A | 6/1937 | Ellis | |
| 2,255,082 A | 9/1941 | Orthner et al. | |
| 2,438,091 A | 3/1948 | Lynch | |
| 2,528,378 A | 10/1950 | Mannheimer | |
| 2,658,072 A | 11/1953 | Kosmin | |
| 2,702,279 A | 2/1955 | Funderburk et al. | |
| 3,070,510 A * | 12/1962 | Broge et al. | 424/52 |
| 3,586,715 A | 6/1971 | Smeets | |
| 3,812,044 A | 5/1974 | Connor et al. | |
| 3,915,903 A | 10/1975 | Wise | |
| 3,929,678 A | 12/1975 | Laughlin et al. | |
| 3,985,668 A * | 10/1976 | Hartman | 510/369 |
| 4,025,444 A | 5/1977 | Murphy et al. | |
| 4,051,056 A | 9/1977 | Hartman | |
| 4,088,620 A | 5/1978 | Nihongi et al. | |
| 4,102,992 A * | 7/1978 | Davis | 424/49 |
| 4,240,919 A * | 12/1980 | Chapman | 510/369 |
| 4,298,490 A | 11/1981 | Lange et al. | |
| 4,309,316 A | 1/1982 | Lange et al. | |
| 4,473,611 A | 9/1984 | Haq | |
| 4,481,126 A | 11/1984 | Trinh et al. | |
| 4,537,604 A | 8/1985 | Dawson | |
| 4,565,644 A * | 1/1986 | Smith et al. | 15/104.93 |
| 4,565,647 A | 1/1986 | Llenado | |
| 4,581,385 A | 4/1986 | Smith et al. | |
| 4,657,692 A | 4/1987 | Choy et al. | |
| 4,663,069 A | 5/1987 | Llenado | |
| 4,676,920 A * | 6/1987 | Culshaw | 510/396 |
| 4,704,233 A | 11/1987 | Hartman et al. | |
| 4,767,563 A * | 8/1988 | de Buzzaccarini | 510/397 |
| 4,772,425 A | 9/1988 | Chirash et al. | |
| 4,842,763 A * | 6/1989 | Troger et al. | 134/4 |
| 4,906,396 A | 3/1990 | Falholt et al. | |
| 5,287,207 A | 2/1994 | Mulkens et al. | |
| 5,500,451 A | 3/1996 | Goldman et al. | |
| 5,776,872 A | 7/1998 | Giret et al. | |
| 5,776,878 A | 7/1998 | Theon | |
| 5,798,505 A | 8/1998 | Lee | |
| 5,821,214 A * | 10/1998 | Weibel | 510/368 |
| 5,830,445 A | 11/1998 | Bouillon et al. | |
| 5,883,062 A | 3/1999 | Addison et al. | |
| 5,898,026 A | 4/1999 | Yianakopoulos et al. | |
| 5,906,973 A | 5/1999 | Ouzounis et al. | |
| 6,008,181 A | 12/1999 | Cripe et al. | |
| 6,020,303 A | 2/2000 | Cripe et al. | |
| 6,060,443 A | 5/2000 | Cripe et al. | |
| 6,080,707 A | 6/2000 | Glenn et al. | |
| 6,132,212 A | 10/2000 | Horiguchi et al. | |
| 6,221,829 B1 | 4/2001 | Symes et al. | |
| 6,242,405 B1 | 6/2001 | Lykke et al. | |
| 2,305,434 A1 | 7/2001 | Luciani et al. | |
| 6,265,363 B1 | 7/2001 | Viscovitz | |
| 6,274,540 B1 | 8/2001 | Scheibel et al. | |
| 6,299,746 B1 | 10/2001 | Conte et al. | |
| 6,306,817 B1 | 10/2001 | Kott et al. | |
| 6,359,031 B1 | 3/2002 | Lykke et al. | |

(Continued)

FOREIGN PATENT DOCUMENTS

| | | |
|---|---|---|
| DE | 24 10 425 A1 | 10/1974 |
| DE | 102004038771 * | 4/2005 |

(Continued)

OTHER PUBLICATIONS

International Search Report; International Application No. PCT/US2010/061233; mailed Apr. 18, 2011; 10 pages.

International Standard; ISO 9276-6:2008(E) section 8.2; section 7; Representation of results of particle size analysis- Part 6: Descriptive and quantitative representation of particle shape and morphology.

ASTM Designation: F1877-05 Jun. 10, 2009; Standard Practice for Characterization of Particles; 14 pages; chapter 11.3.6; Section 11.3.2.

International Standard; ISO 9276-6:2008(E) section 8.2; section 7; Representation of results of particle size analysis- Part 6: Descriptive and quantitative representation of particle shape and morphology, Sep. 2008.

(Continued)

*Primary Examiner* — Charles Boyer

(74) *Attorney, Agent, or Firm* — John T. Dipre; Steven W. Miller

(57) ABSTRACT

The present invention relates to a liquid, cleaning and/or cleansing composition comprising abrasive cleaning particles.

14 Claims, 1 Drawing Sheet

(56) References Cited

U.S. PATENT DOCUMENTS

| | | |
|---|---|---|
| 6,369,121 B1 | 4/2002 | Catalfamo et al. |
| 6,444,716 B1 | 9/2002 | Hird et al. |
| 6,514,926 B1 | 2/2003 | Kott et al. |
| 6,525,233 B1 | 2/2003 | Connor et al. |
| 6,537,957 B1 | 3/2003 | Cardola et al. |
| 6,566,319 B1 | 5/2003 | Scheibel et al. |
| 6,583,096 B1 | 6/2003 | Kott et al. |
| 6,593,285 B1 | 7/2003 | Scheibel et al. |
| 6,602,840 B1 | 8/2003 | Scheibel et al. |
| 6,699,963 B2 | 3/2004 | Noda et al. |
| 6,749,066 B2 | 6/2004 | Bergman |
| 6,759,377 B2 | 7/2004 | Hackenthal et al. |
| 6,767,878 B1 | 7/2004 | Paye et al. |
| 6,808,759 B1 | 10/2004 | Okumura et al. |
| 6,858,216 B2 | 2/2005 | Schulze zur Wiesche et al. |
| 1,797,947 A1 | 6/2007 | Anastasiou et al. |
| 2,384,243 A1 | 12/2007 | Cook et al. |
| 7,393,820 B2 * | 7/2008 | Soldanski et al. ............. 510/483 |
| 7,713,921 B2 | 5/2010 | Boutique et al. |
| 7,994,111 B2 | 8/2011 | Caggioni et al. |
| 2002/0137647 A1 * | 9/2002 | Hackenthal et al. .......... 510/180 |
| 2002/0166832 A1 | 11/2002 | Silud et al. |
| 2002/0173243 A1 | 11/2002 | Costas et al. |
| 2003/0176633 A1 | 9/2003 | Noda et al. |
| 2003/0215417 A1 | 11/2003 | Uchiyama et al. |
| 2004/0216388 A1 | 11/2004 | Mathur et al. |
| 2004/0266645 A1 | 12/2004 | Albrecht et al. |
| 2005/0065056 A1 * | 3/2005 | Cook et al. .................... 510/438 |
| 2005/0130873 A1 * | 6/2005 | Cheung et al. ................ 510/507 |
| 2005/0170979 A1 | 8/2005 | Massaro et al. |
| 2005/0201965 A1 | 9/2005 | Kuhlman et al. |
| 2006/0011885 A1 * | 1/2006 | Christmas et al. ......... 252/186.1 |
| 2006/0094635 A1 | 5/2006 | Pereira |
| 2006/0177488 A1 | 8/2006 | Caruso et al. |
| 2007/0006391 A1 | 1/2007 | Ghosh et al. |
| 2007/0010415 A1 | 1/2007 | Kinscherf et al. |
| 2007/0041927 A1 | 2/2007 | Blaeser et al. |
| 2007/0043147 A1 | 2/2007 | Higgins et al. |
| 2007/0135645 A1 | 6/2007 | Ignatyev et al. |
| 2007/0167345 A1 | 7/2007 | Soldanski et al. |
| 2007/0191256 A1 | 8/2007 | Fossum et al. |
| 2007/0270730 A1 | 11/2007 | Rische et al. |
| 2008/0013972 A1 | 1/2008 | De Almeida et al. |
| 2008/0108714 A1 | 5/2008 | Swazey et al. |
| 2008/0139433 A1 | 6/2008 | Mock et al. |
| 2008/0149137 A1 | 6/2008 | Steinbrenner et al. |
| 2008/0248144 A1 | 10/2008 | Guenter et al. |
| 2009/0176935 A1 | 7/2009 | Boeckh et al. |
| 2009/0253816 A1 | 10/2009 | Nascimento et al. |
| 2009/0291306 A1 | 11/2009 | Quadbeck-Seeger |
| 2009/0325837 A1 | 12/2009 | Mundschau et al. |
| 2010/0081604 A1 | 4/2010 | Barger et al. |
| 2010/0081605 A1 | 4/2010 | Barger et al. |
| 2010/0081606 A1 | 4/2010 | Barger et al. |
| 2010/0197553 A1 | 8/2010 | Barnabas et al. |
| 2011/0021398 A1 | 1/2011 | Allef et al. |
| 2011/0039744 A1 | 2/2011 | Heath et al. |
| 2011/0150787 A1 | 6/2011 | Gonzales et al. |
| 2011/0150788 A1 | 6/2011 | Gonzales et al. |
| 2011/0150949 A1 | 6/2011 | Gonzales et al. |
| 2011/0150951 A1 | 6/2011 | Gonzales et al. |
| 2011/0178196 A1 | 7/2011 | Steinke et al. |
| 2011/0189414 A1 | 8/2011 | Whitehouse |
| 2011/0262371 A1 | 10/2011 | Deleersnyder et al. |
| 2011/0262504 A1 | 10/2011 | Deleersnyder et al. |
| 2011/0287105 A1 | 11/2011 | Gittleman |
| 2012/0029519 A1 | 2/2012 | Sengun et al. |
| 2012/0066851 A1 | 3/2012 | Gonzales et al. |
| 2012/0071378 A1 | 3/2012 | Gonzales et al. |
| 2012/0071379 A1 | 3/2012 | Gonzales et al. |
| 2012/0071380 A1 | 3/2012 | Gonzales et al. |
| 2012/0071383 A1 | 3/2012 | Perez-Prat Vinuesa et al. |
| 2012/0202730 A1 | 8/2012 | Allef et al. |

FOREIGN PATENT DOCUMENTS

| | | |
|---|---|---|
| DE | 10 2004 03877 A1 | 8/2005 |
| DE | 10 2004 038771 A1 | 8/2005 |
| DE | 10 2005 023801 A1 | 11/2006 |
| EP | 0 226 723 A2 | 7/1987 |
| EP | 0 957 156 A1 | 11/1999 |
| EP | 1 136 063 A2 | 9/2001 |
| EP | 1 460 125 A1 | 9/2004 |
| GB | 2 001 099 A | 1/1979 |
| GB | 2 126 999 A | 4/1984 |
| GB | 2 145 729 A | 4/1985 |
| GB | 2 184 454 A | 6/1987 |
| JP | A-S54-154410 | 12/1979 |
| JP | 59192526 A | 10/1984 |
| JP | 10025239 A | 1/1998 |
| JP | 2005 296822 A | 10/2005 |
| JP | 2007 077311 A | 3/2007 |
| JP | 2009 160717 A | 7/2009 |
| WO | WO 91/14420 A1 | 10/1991 |
| WO | WO 99/05084 A1 | 2/1999 |
| WO | WO 99/52500 A1 | 10/1999 |
| WO | WO 01/09279 A1 | 2/2001 |
| WO | 01/30315 * | 5/2001 |
| WO | 01/31110 * | 5/2001 |
| WO | WO 01/30315 A1 | 5/2001 |
| WO | WO 01/31110 A1 | 5/2001 |
| WO | 02/38720 * | 5/2002 |
| WO | WO 02/38720 A1 | 5/2002 |
| WO | 03/043599 * | 5/2003 |
| WO | WO 03/043599 A1 | 5/2003 |
| WO | WO 2004/071483 A1 | 8/2004 |
| WO | WO 2004/083328 A2 | 9/2004 |
| WO | WO 2008/006736 A1 | 1/2008 |
| WO | WO 2008/109270 A1 | 9/2008 |

OTHER PUBLICATIONS

"Vegetable Ivory", W.P. Armstrong, (http://waynesword.palomar.edu/pljan99.htm), Jan. 1999.
"Phytelephas", Wikipedia.org (http://en.wikipedia.org/wiki/Phytelephas).
U.S. Appl. No. 13/517,837, filed Jun. 14, 2012, Gonzales, et al.
U.S. Appl. No. 13/517,728, filed Jun. 14, 2012, Gonzales, et al.
U.S. Appl. No. 13/526,592, filed Jun. 19, 2012, Gonzales, et al.
U.S. Appl. No. 13/526,596, filed Jun. 19, 2012, Gonzales, et al.
U.S. Appl. No. 13/517,746, filed Jun. 14, 2012, Gonzales, et al.
U.S. Appl. No. 13/526,605, filed Jun. 19, 2012, Gonzales, et al.
U.S. Appl. No. 13/526,613, filed Jun. 19, 2012, Gonzales, et al.
U.S. Appl. No. 13/517,762, filed Jun. 14, 2012, Perez-Prat Vinuesa, et al.
U.S. Appl. No. 13/621,858, filed Sep. 18, 2012, Gonzales, et al.
U.S. Appl. No. 13/621,860, filed Sep. 18, 2012, Perez-Prat Vinuesa, et al.

\* cited by examiner

A = the surface area of the particle

A(0.8) = the surface area of the projection of all inscribed discs having diameter ranging from Dmax to 0.8xDmax

US 8,680,036 B2

LIQUID CLEANING COMPOSITION COMPRISING COLOR-STABLE POLYURETHANE ABRASIVE PARTICLES

CROSS-REFERENCES TO RELATED APPLICATIONS

This application claims the benefit of U.S. Provisional Application No. 61/288,887 filed Dec. 22, 2009; and U.S. Provisional Application No. 61/326,286, filed Apr. 21, 2010; and U.S. Provisional Application No. 61/326,290, filed Apr. 21, 2010.

TECHNICAL FIELD

The present invention relates to liquid compositions for cleaning and/or cleansing a variety of inanimate and animate surfaces, including hard surfaces in and around the house, dish surfaces, teeth hard and soft tissue surface of the oral cavity, such as teeth, gums, tongue and buccal surfaces, human and animal skin, car and vehicles surfaces, etc. More specifically, the present invention relates to liquid scouring compositions comprising suitable particles for cleaning and/or cleansing.

BACKGROUND OF THE INVENTION

Scouring compositions such as particulate compositions or liquid (incl. gel, paste-type) compositions containing abrasive components are well known in the art. Such compositions are used for cleaning and/or cleansing a variety of surfaces; especially those surfaces that tend to become soiled with difficult to remove stains and soils.

Amongst the currently known scouring compositions, the most popular ones are based on abrasive particles with shapes varying from spherical to irregular. The most common abrasive particles are either inorganic like carbonate salt, clay, silica, silicate, shale ash, perlite and quartz sand or organic polymeric beads like polypropylene, PVC, melamine, urea, polyacrylate and derivatives, and come in the form of liquid composition having a creamy consistency with the abrasive particles suspended therein.

The surface safety profile of such currently known scouring compositions is inadequate alternatively, poor cleaning performances is shown for compositions with an adequate surface safety profile. Indeed, due to the presence of very hard abrasive particles, these compositions can damage, i.e., scratch, the surfaces onto which they have been applied. Indeed, the formulator needs to choose between good cleaning/cleansing performance but featuring strong surface damage or compromising on the cleaning/cleansing performance while featuring an acceptable surface safety profile. In addition, such currently known scouring compositions at least in certain fields of application (e.g., hard surface cleaning) are perceived by consumers as outdated.

It is thus an objective of the present invention to provide a liquid cleaning and/or cleansing composition suitable to clean/cleanse a variety of surfaces, including inanimate and animate surfaces, such hard surfaces in and around the house, dish surfaces, hard and soft tissue surface of the oral cavity, such as teeth, gums, tongue and buccal surfaces, human and animal skin, etc., wherein the composition provides good cleaning/cleansing performance, whilst providing a good surface safety profile.

It has been found that the above objective can be met by the composition according to the present invention.

It is an advantage of the compositions according to the present invention that they may be used to clean/cleanse inanimate and animate surfaces made of a variety of materials like glazed and non-glazed ceramic tiles, enamel, stainless steel, Inox®, Formica®, vinyl, no-wax vinyl, linoleum, melamine, glass, plastics, painted surfaces, human and animal skin, hair, hard and soft tissue surface of the oral cavity, such as teeth enamel, gums, tongue and buccal surfaces, and the like.

A further advantage of the present invention is that in the compositions herein, the particles can be formulated at very low levels, whilst still providing the above benefits. Indeed, in general for other technologies, high levels of abrasive particles are needed to reach good cleaning/cleansing performance, thus leading to high formulation and process cost, difficult rinse and end cleaning profiles, as well as limitation for aesthetics and a pleasant hand feel of the cleaning/cleansing composition.

SUMMARY OF THE INVENTION

The present invention is directed to a liquid cleaning and/or cleansing composition comprising abrasive cleaning particles, wherein said abrasive cleaning particles have been reduced from a foam via grinding or milling, and wherein said foam has a density from 5 kg/m$^3$ to 150 kg/m$^3$, and wherein said foam has a cell size from 40 micrometers to 700 micrometers.

The present invention further encompasses a process of cleaning and/or cleansing a surface with a liquid, cleaning and/or cleansing composition comprising abrasive cleaning particles, wherein said surface is contacted with said composition, preferably wherein said composition is applied onto said surface.

DETAILED DESCRIPTION OF THE INVENTION

The Liquid Cleaning/Cleansing Composition

Figure 1:
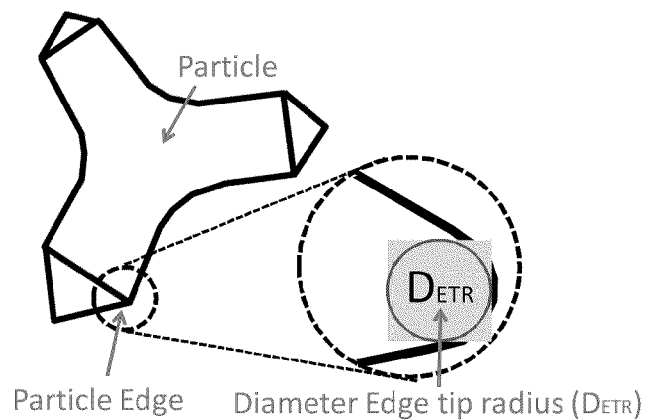
FIG. 1 is drawing showing an illustration how to calculate the tip radius.

The compositions according to the present invention are designed as cleaners/cleansers for a variety of inanimate and animate surfaces. Preferably, the compositions herein are suitable for cleaning/cleansing surfaces selected from the group consisting of inanimate surfaces and animate surfaces.

In a preferred embodiment, the compositions herein are suitable for cleaning/cleansing inanimate surfaces selected from the group consisting of household hard surfaces; dish surfaces; surfaces like leather or synthetic leather; and automotive vehicle surfaces.

In a highly preferred embodiment, the compositions herein are suitable to clean household hard surfaces.

By "household hard surface", it is meant herein any kind of surface typically found in and around houses like kitchens, bathrooms, e.g., floors, walls, tiles, windows, cupboards, sinks, showers, shower plastified curtains, wash basins, WCs, fixtures and fittings and the like made of different materials like ceramic, vinyl, no-wax vinyl, linoleum, melamine, glass, Inox®, Formica®, any plastics, plastified wood, metal or any painted or varnished or sealed surface and the like. Household hard surfaces also include household appliances including, but not limited to refrigerators, freezers, washing machines, automatic dryers, ovens, microwave ovens, dishwashers and so on. Such hard surfaces may be found both in private households as well as in commercial, institutional and industrial environments.

By "dish surfaces" it is meant herein any kind of surfaces found in dish cleaning, such as dishes, cutlery, cutting boards, pans, and the like. Such dish surfaces may be found both in private households as well as in commercial, institutional and industrial environments.

In an another preferred embodiment, the compositions herein are suitable for cleaning/cleansing animate surfaces selected from the group consisting of human skin; animal skin; human hair; animal hair; and teeth.

The compositions according to the present invention are liquid compositions as opposed to a solid or a gas. Liquid compositions include compositions having a water-like viscosity as well as thickened compositions, such as gels and pastes.

In a preferred embodiment herein, the liquid compositions herein are aqueous compositions. Therefore, they may comprise from 65% to 99.5% by weight of the total composition of water, preferably from 75% to 98% and more preferably from 80% to 95%.

In another preferred embodiment herein, the liquid compositions herein are mostly non-aqueous compositions although they may comprise from 0% to 10% by weight of the total composition of water, preferably from 0% to 5%, more preferably from 0% to 1% and most preferably 0% by weight of the total composition of water.

In a preferred embodiment herein, the compositions herein are neutral compositions, and thus have a pH, as is measured at 25° C., of 6-8, more preferably 6.5-7.5, even more preferably 7.

In other preferred embodiment compositions have pH preferably above pH 4 and alternatively have pH preferably below pH 9.

Accordingly, the compositions herein may comprise suitable bases and acids to adjust the pH.

A suitable base to be used herein is an organic and/or inorganic base. Suitable bases for use herein are the caustic alkalis, such as sodium hydroxide, potassium hydroxide and/or lithium hydroxide, and/or the alkali metal oxides such, as sodium and/or potassium oxide or mixtures thereof. A preferred base is a caustic alkali, more preferably sodium hydroxide and/or potassium hydroxide.

Other suitable bases include ammonia, ammonium carbonate, all available carbonate salts such as $K_2CO_3$, $Na_2CO_3$, $CaCO_3$, $MgCO_3$, etc., alkanolamines (as e.g. monoethanolamine), urea and urea derivatives, polyamine, etc.

Typical levels of such bases, when present, are of from 0.01% to 5.0% by weight of the total composition, preferably from 0.05% to 3.0% and more preferably from 0.1% to 0.6%.

The compositions herein may comprise an acid to trim its pH to the required level, despite the presence of an acid, if any, the compositions herein will maintain their preferably neutral pH as described herein above. A suitable acid for use herein is an organic and/or an inorganic acid. A preferred organic acid for use herein has a pKa of less than 6. A suitable organic acid is selected from the group consisting of citric acid, lactic acid, glycolic acid, succinic acid, glutaric acid and adipic acid and a mixture thereof. A mixture of said acids may be commercially available from BASF under the trade name Sokalan® DCS. A suitable inorganic acid is selected from the group consisting hydrochloric acid, sulphuric acid, phosphoric acid and a mixture thereof.

A typical level of such an acid, when present, is of from 0.01% to 5.0% by weight of the total composition, preferably from 0.04% to 3.0% and more preferably from 0.05% to 1.5%.

In a preferred embodiment according to the present invention the compositions herein are thickened compositions. Preferably, the liquid compositions herein have a viscosity of up to 7500 cps at $20\ s^{-1}$, more preferably from 5000 cps to 50 cps, yet more preferably from 2000 cps to 50 cps and most preferably from 1500 cps to 300 cps at $20\ s^{-1}$ and 20° C. when measured with a Rheometer, model AR 1000 (Supplied by TA Instruments) with a 4 cm conic spindle in stainless steel, 2° angle (linear increment from 0.1 to 100 $sec^{-1}$ in max. 8 minutes).

In another preferred embodiment according to the present invention the compositions herein have a water-like viscosity. By "water-like viscosity" it is meant herein a viscosity that is close to that of water. Preferably the liquid compositions herein have a viscosity of up to 50 cps at 60 rpm, more preferably from 0 cps to 30 cps, yet more preferably from 0 cps to 20 cps and most preferably from 0 cps to 10 cps at 60 rpm and 20° C. when measured with a Brookfield digital viscometer model DV II, with spindle 2.

Abrasive Cleaning Particles

The liquid cleaning and/or cleansing composition herein comprise abrasive cleaning particles that are selected or synthesized to feature very effective shapes, e.g. defined by macroshape and mesoshape descriptors whereas effective shape of particles are obtained by reducing a foam material into particles.

The applicant has found that non-rolling and sharp abrasive cleaning particles provide good soil removal and low surface damage. The applicant has found that very specific particle shapes can be obtained from foam structures and incidentally, the shape of the resulting particles promote effective sliding of the abrasive particles vs. more typical abrasive particles e.g. produced from un-foamed material where rolling movement is rather promoted and is less effective in displacing soil from the surface. Therefore it is the object of this invention to synthesize and select carefully the abrasive accordingly to its shape and especially, it is the object of this invention to describe the foam structure and the process to reduce foam into efficient particles.

The applicant has found that non-rolling and sharp abrasive cleaning particles provide good soil removal and low surface damage. Indeed the applicant has found that very specific particle shapes, e.g. defined by circularity, promote effective sliding of the abrasive particles vs. typical abrasive particles, where rolling movement is rather promoted and which are less effective in displacing soil from the surface.

Additionally, the abrasive particles have preferably a multitude of sharp edges which are typical features of particles produced from foam structures defined by the present invention. The sharp edges of the non-spherical particles are defined by edges having a tip radius below 20 µm, preferably below 8 µm, most preferably from 5 µm to 0.5 µm. The tip radius is defined by the diameter of an imaginary circle fitting the curvature of the edge extremity. The applicant has found that particles obtained from grinding foams typically feature particles with sharp edges that are the result of the foaming process. Blowing agents, either gas or volatilized solvent optionally with/without addition of tensioactifs or polymeric agents, help during the foaming process to sharpen the foam material edges (or struts) owing to the curvature of the expanding bubble.

FIG. 1. is an illustration of tip radius.

The abrasive particles are composed of the same foam material from which they are produced. Incidentally, the abrasive material may be produced from organic foams and even from mineral foams although pragmatically mineral foams are less common unless mineral materials are co-foamed, e.g.: as filler in a typical foaming process with otherwise known foamable organic or polymeric materials. Similarly, non-mineral abrasive material can also be co-foamed with otherwise known foamable organic or polymeric materials. In the most simple and common case, the abrasive raw material per se—e.g.: mineral or non-mineral filler—is dispersed within a matrix prior to undergoing the foaming process to achieve the adequate foam structure. In that case, the material used as filler in foaming processes is typically—without being exhaustive—e.g.: organic or inorganic salt abrasives such as carbonate-derived salts, phosphate-derived salts, pyrophosphate-derived salts, silica or alumina derived salts, hydroxyapatite, diatomaceous, fuller earth, talc, etc., polymeric material derived from polyethylene, polypropylene, PVC, polycarbonate, melamine, urea, polyurethane, polyacrylate, polystyrene, phenolic, polyesters, polyamide, or natural material derived from cellulose, lingo-cellulose or shell, such as nut shell, kernel, wood, bamboo, plants, etc.

Preferably the abrasive particles are made from the polymeric material selected from the group consisting' of polyethylene, polypropylene, PVC, polycarbonate, melamine, urea, polyurethane, polyacrylate, polystyrene, phenblic, polyesters, polyamide and mixtures thereof and natural abrasives derived from cellulose, lingo-cellulose or shell such as nut shell, apple seeds, olive stones, apricot seed, kernel, wood, bamboo and plants and mixtures thereof. More preferably the abrasive particles are made from the polymeric material selected from the group consisting of polyethylene, polypropylene, PVC, polycarbonate, melamine, urea, polyurethane, polyacrylate, polystyrene, phenolic, polyesters, polyamide and mixtures thereof. Even more preferably the abrasive particles are made polymeric from polyurethane, polyester, polyacrylate, polystyrene and mixtures thereof. Most preferably the abrasive particles are made from the rigid polyurethane foam made from the diisocyanate (e.g. Lupranate M200R or Lupranate M20S) and diol (Lupranol 3423).

In a preferred embodiment, the foaming material is used without filler and presents sufficient abrasive properties after it has been foamed and reduced after foaming into abrasive particles.

Foaming processes and foam structures are typically achieved via a gas expansion process, e.g.: either by injecting gas or solvent within the abrasive precursor and allowing expansion by pressure drop and/or increase of temperature, e.g.: extrusion foaming process. In that case, thermoplastic material in a form of pure polymer or polymer blend or plasticized polymers etc. are usually used. Typical examples of thermoplastic polymers are, without being exhaustive: polyethylene, polypropylene, PVC, polycarbonate, polyurethane, polyacrylate, polystyrene, polyesters, polyamide, etc. Lists of alternative thermoplastic polymers can be found in extrusion foaming or gas foaming literature (for examples see the books "Thermoplastic Foam Extrusion" by James L. Throne or "Foam Extrusion: Principles and Practice by Shau-Tarng Lee). Typical gases used in such processes are air, nitrogen, carbon dioxide or organic solvents such as pentane, cyclopentane, etc with or without inclusion of nucleation and foam stabilizing agents. In most cases, a controlled amount of gas is allowed to dissolve into the polymer/polymeric mix into in melted phase whereas the skilled operator can control accurately the foaming parameters e.g.: formulation, time/temperature/pressure cycle parameters to target specific foam structures.

Foaming processes and foam structures are also typically achieved via emulsion foaming of monomers followed by a hardening step via chemical, heat or radiative, e.g.: UV, curing and if necessary followed by a drying step of the solidified foam. Several monomer types are possible to use e.g.: those derived from the non-exhaustive list of the following monomer structures e.g.: vinyl, styrene, acrylate, methacrylate, diene, etc. Examples of materials and foaming and curing process are extensively described in literature (e.g.: refer to the book "Emulsion Polymer Technology" by Robert D. Athey). A preferred route for production of the foam is to form a water/oil High Internal Phase Emulsion of water in the monomer mixture and polymerize in-situ, as described in U.S. Pat. No. 6,369,121 to Catalfamo et al, incorporated by reference herein. In a preferred embodiment the foam is produced after polymerization of a divinyl benzene cross-linked styrene polymer using a water/oil High internal Phase Emulsion process. After curing, the foam is then reduced to particles via a grinding or milling operation.

Foaming processes and foam structures are also typically achieved by mechanical agitation e.g.; battering of a viscous mix e.g.: typically including protein with emulsifying and possibly stabilizing features followed by a step of curing/hardening and if necessary drying of the solidified foam. Non-exhaustive examples of proteins are white egg or pure albumen, gelatin, saponin, gluten, soybean protein, globulin, prolamine, glutelin, histone, protamine, etc. whereas the proteins are often agitated in presence of water, emulsifying agent, stabilizers e.g.: alginic acid, and, very desirably, a significant amount of polymerizable monomer and/crosslinker to achieve sufficient hardness of the foam. For further reference refer to the book "Functionality of Proteins in Food" by Joseph F. Zayas, "Protein Functionality in Food Systems" from Hettiarachchy, Article in Journal of Cereal science 47 (2008) 233-238 by E. Zukowska et Al; or US2006/0065159.

Particularly preferred foaming processes and foam structures are also typically achieved by simultaneous polymerization, with or without crosslinking of monomers, coupled with in-situ production of expanding gas. Such a process is typically used to produce polyurethane foam. Processes, polyurethane precursors, formulations, additives, etc. are abundantly described in literature as well as, most conveniently, their impact on the various critical foam structure parameters, such as foam density, cell size, content of closed cell, strut aspect ratio and to some extent foam and particle hardness, which are objects of the present invention in producing cleaning particles with effective shapes. Much information on polyurethane formulation and production processes is available in literature (see for reference following the books: "Rigid polyurethane/polyisocyanurate foam processing" by Robert Wood "Polyurethane and Related Foams: Chemistry and Technology" by Kaneyoshi Ashida and "Chemistry and technology of polyols for polyurethanes" by Mihail Ionescu).

The applicant has found that efficacious and safe cleaning particles can be produced from foams with very specific structural parameters as described below. Indeed the applicant has found that the structure of the foam allows the shape parameters of the cleaning particles to be controlled and the applicant has demonstrated that the particle shape parameters greatly impact the cleaning performance of the particles. It is understood that the foam structural parameters described below have a direct impact on the desired particle shape after grinding of the foam into abrasive particles; hence the accurate control of the foam structure is a preferred and convenient means to synthesized efficient abrasive particles.

Foam Density:

The applicant has found that a good cleaning effect can be achieved with abrasive particles which have been made from foam having a density above 100 kg/m$^3$, and even up to 500 kg/m$^3$. However the applicant has surprisingly found that a significantly better cleaning effect can be achieved with a foam density below 100 kg/m$^3$, more preferably with a foam density from 50 kg/m$^3$ to 100 kg/m$^3$ and most preferably with a foam density from 5 kg/m$^3$ to 50 kg/m$^3$. Foam density can be measured, for instance, using the protocol described in ASTM D3574.

Foam Cell Size:

Similarly, the applicant has found that a good cleaning effect can be achieved with abrasive particles which have been made from foams featuring cell sizes ranging from 20 micrometers to 2000 micrometers. However the applicant has surprisingly found that a significantly better cleaning effect can be achieved with foams featuring cell sizes between 100-1000 micrometers, more preferably from 200 to 500 micrometers and most preferably from 300 to 450 micrometers. Foam cell size can be measured for instance using the protocol described in ASTM D3576.

Foam Closed Cell Content:

Similarly, the applicant has found that a good cleaning effect can be achieved with abrasive particles which have been made from foams featuring close-cell structures. However, the applicant has surprisingly found that a significantly better cleaning effect can be achieved with abrasive cleaning particles, which have been reduces into particles from foams with open-cell structure. An open-cell foam structure presents the opportunity to form well defined sharp struts, which in turn produce effective abrasive particles. On the contrary, the presence of closed cells, wherein each cell is closed by foam material extending from each strut into a membrane-like material, produce after grinding into abrasive particles an abrasive population that contains a fraction of flat-shaped residue. This flat-shaped residue is not providing effective cleaning performance, and therefore, is undesirable feature. The shape of this flat-shaped residue is sub-optimal to deliver cleaning. Additionally, these membranes are inherently very fragile and are easily broken into significantly small particles, including undesirable dust, with sizes ranging from several hundred micrometers to sub-micrometer sizes during the grinding of the foam and also during use in the cleaning process. The applicant has found that foam structures with less than 50%, preferably less than 30%, and most preferably less than 15% of closed cells are desirable in producing effective abrasive cleaning particles.

Foam Strut Aspect Ratio:

Similarly, the applicant has found that a good cleaning effect can be achieved with abrasive particles which have been made from the foams featuring struts with high aspect ratios. By struts, the applicant defines the elongated material that interconnect to form the cellular structure of the foam, which is best described as a pentagonal dodecahedron structure for the foams with density typically between 5 and 50 kg/m$^3$ targeted herein. The strut length (L) is typically counted as the distance between the geometrical centers of 2 interconnecting knots. The struts thickness (T) is typically the projected strut thickness at the middle of the strut length. The applicant has understood that particles that are derived from foam presenting struts with excessively small L/T ratio present sub-optimal shapes for cleaning since likely to produce rounder particles that readily roll. On the contrary, the particles that are derived from foam presenting struts with excessively high L/T ratio also present sub-optimal shape for cleaning since they are likely to produce excessive amount of rod-like particles featuring low soil removal. Incidentally, the applicant has surprisingly found that significantly better cleaning effect can be achieved with struts having an L/T ratio ranging from 1.5 to 10, preferably from 2.0 to 8.0 and more preferably from 3.0 to 6.0 and most preferred from 3.5 to 4.5 as defined by Visiocell software.

Figure 2:
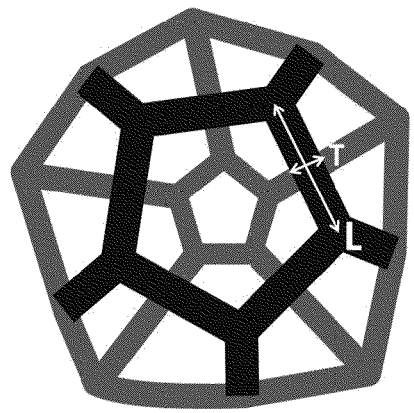
FIG. 2 is drawing showing an illustration how to calculate foam strut aspect ratio.

FIG. 2 Pentagonal dodecahedron structure with struts length (L) and thickness (T) In a preferred embodiment, in order to favor the reduction of the foam into particles, the foam is sufficiently brittle, i.e. upon stress, the foam has little tendency to deform but rather will break into particles.

Efficient cleaning particles are therefore produced by grinding the foam structure with special care to target size and shape. Hence for instance, when large particle size is desired, foam with large cell size is desirable and vice-et-versa. Additionally, in order to preserve an optimal particle shape while grinding the foam structure, it is recommended to not target particle size excessively below the dimension of the cell size of the foam. Typically, the applicant recommends targeting particle size not below about half of the foam cell size. The applicant has found that excessive particle reduction e.g.: vis-à-vis the original foam structure and especially vis-à-vis the cell size yields rounder particles with sub-optimal cleaning efficiency.

In practice, the process to reduce the foam into particle population is set such as the amount of particles with size below half of the average foam cell size is below 30% by weight, preferably below 20% more preferably below 10% and most preferably no particles are detected, whereas the particle size weight proportion is defined by physical sieving method. Note: In order to proceed to the separation of the particles based on size related to half of the average foam cell size, a tolerance of 10% is accepted for the selection of the sieving mesh vis-a-vis the theoretical target sieving grid. The selected sieving mesh tolerance is valid for smaller available sieving mesh vs. the theoretical target size.

One suitable way of reducing the foam to the abrasive cleaning particles herein is to grind or mill the foam. Other suitable means include the use of eroding tools such as a high speed eroding wheel with dust collector wherein the surface of the wheel is engraved with a pattern or is coated with abrasive sandpaper or the like to promote the foam to form the abrasive cleaning particles herein.

Alternatively and in a highly preferred embodiment herein, the foam may be reduced to particles in several stages. First the bulk foam can be broken into pieces of a few cm dimensions by manually chopping or cutting, or using a mechanical tool such as a lumpbreaker, for example the Model 2036 from S Howes, Inc. of Silver Creek, N.Y.

In a highly preferred embodiment herein, in order to achieve the geometrical shape descriptors of the abrasive cleaning particles (i.e. solidity, circularity and/or roughness) the abrasive cleaning particles are obtained from foamed polymeric material, which is reduced into the abrasive particles preferably by grinding or milling as described herein later on.

Hardness of the Abrasive Particles:

Preferred abrasive cleaning particles suitable for used herein are hard enough to provide good cleaning/cleansing performance, whilst providing a good surface safety profile.

The hardness of the abrasive particles reduced from the foam can be modified by changing the raw material used to prepare the foam. For example modification of the hardness of the polyurethane foam is possible via several ways. For example, without being exhaustive, the selection of the diisocyanate and especially the selection of the isocyanate with high functionality e.g.: >2, preferably >2.5, most preferably above 2.7, increases the polyurethane hardness. Similarly, the use of low molecular weight polyols e.g.: <4000 Mw, preferably <2000 Mw and most preferably below 1000 Mw also increase the polyurethane hardness. More importantly is the balance diisocyanate/polyols in the reaction mixture, although excess of diisocyanate also increase the foam hardness. Another possibility to increase hardness is to introduce a small molecular weight crosslinker. Alternatively selection of catalyst, will promote the formation of urea bond, is additional way to increase the foam hardness.

Preferred abrasive cleaning particles in the present invention have hardness from 3 to 50 kg/mm$^2$, preferably from 4 to 25 kg/mm$^2$ and most preferably from 5 to 15 kg/mm$^2$ on the HV Vickers hardness.

Vickers Hardness Test Method:

Vickers hardness HV is measured at 23° C. according to standard methods ISO 14577-1, ISO 14577-2, ISO 14577-3.The Vickers hardness is measured from a solid block of the raw material at least 2 mm in thickness. The Vickers hardness micro indentation measurement is carried out by using the Micro-Hardness Tester (MHT), manufactured by CSM Instruments SA, Peseux, Switzerland.

As per the ISO 14577 instructions, the test surface should be flat and smooth, having a roughness (Ra) value less than 5% of the maximum indenter penetration depth. For a 200 μm maximum depth this equates to a Ra value less than 10 μm. As per ISO 14577, such a surface may be prepared by any suitable means, which may include cutting the block of test material with a new sharp microtome or scalpel blade, grinding, polishing or by casting melted material onto a flat, smooth casting form and allowing it to thoroughly solidify prior testing.

Suitable general settings for the Micro-Hardness Tester (MHT) are as follows:
Control mode: Displacement, Continuous
Maximum displacement: 200 μm
Approach speed: 20 nm/s
Zero point determination: at contact
Hold period to measure thermal drift at contact: 60 s
Force application time: 30 s
Frequency of data logging: at least every second
Hold time at maximum force: 30 s
Force removal time: 30 s
Shape/Material of intender tip: Vickers Pyramid Shape/Diamond Tip Alternatively, the abrasive cleaning particles in the present invention hardness may also expressed accordingly to the MOHS hardness scale. Preferably, the MOHS hardness is comprised between 0.5 and 3.5 and most preferably between 1 and 3.The MOHS hardness scale is an internationally recognized scale for measuring the hardness of a compound versus a compound of known hardness, see Encyclopedia of Chemical Technology, Kirk-Othmer, 4 th Edition Vol 1, page 18 or Lide, D. R (ed) CRC Handbook of Chemistry and Physics, 73 rd edition, Boca Raton, Fla.: The Rubber Company, 1992-1993.Many MOHS Test kits are commercially available containing material with known MOHS hardness. For measurement and selection of abrasive material with selected MOHS hardness, it is recommended to execute the MOHS hardness measurement with un-shaped particles e.g.: with spherical or granular forms of the abrasive material since MOHS measurement of shape particles will provide erroneous results.

In order to control that the foam-derived particles feature effective shape, it is useful in the present invention to define shape method and critical shape target parameters The shape of the abrasive cleaning particle can be defined in many ways. The present invention defines cleaning particle shape in a form of particle, which reflects the geometrical proportions of a particle and more pragmatically of a particles population. Very recent analytical techniques allow an accurate simultaneous measurement of particle shape from a large number of particles, typically greater than 10000 particles (preferably above 100 000). This enables accurate tuning and/or selection of average particle population shape with discriminative performance. These measurements analyse of particle shape are conducted using Occhio Nano 500 Particle Characterisation Instrument with its accompanying software Callistro version 25 (Occhio s.a. Liege, Belgium). This instrument is used to prepare, disperse, image and analyse the particle samples, as per manufacturer's instructions, and the following instrument setting selections: White Requested=180, vacuum time=5000 ms, sedimentation time=5000 ms, automatic threshold, number of particles counted/analyses=8000 to 500000, minimum number of replicates/sample=3, lens setting 1×/1.5×.

The applicant has considered although that the shape of particle of significant size play a critical role so in practice, the shape parameter are measured as mean shape of a particle population after exclusion of particles with size lower than 10 micrometers. Exclusion can be done either physically with help of sieve or preferably electronically via statistic filtering of particles with size diameter e.g.: "Area diameter" (the value of the diameter of a disc that has the same area A as the particle), below 10 micrometers (cf. ISO 9276-6:2008(E) section 7)

In the present invention shape descriptors are calculations of geometrical descriptors/shape factors. Geometrical shape factors are ratios between two different geometrical properties, such properties are usually a measure of proportions of the image of the whole particle or a measure of the proportions of an ideal geometrical body enveloping the particle or forms an envelope around the particle. These results are macroshape descriptors similar to aspect ratio, however the Applicant has discovered that mesoshape descriptors—a specific sub-class of macroshape descriptor—are particularly critical to the cleaning effectiveness and surface safety performances of the abrasive cleaning particles, while more typical shape parameters such as aspect ratio was proved insufficient. These mesoshape descriptors are a great help in defining how different a particle is compared to an ideal geometrical shape, especially how different compared to a sphere, and incidentally help define its ability for non-rolling, e.g.: sliding, effective cleaning movement pattern. The abrasive cleaning particles of the present invention are different from typical spherical or spherical-resembling e.g.: granular, abrasives forms.

Roughness

Roughness is a quantitative, 2-dimensional image analysis shape description, and is being measured according to ISO 9276-6:2008(E) section 8.2 as implemented via the Occhio Nano 500 Particle Characterisation Instrument with its accompanying software Callistro version 25 (Occhio s.a. Liege, Belgium). Roughness defines 2D measurements, the equivalent useful surface area outside of the core surface area of the particle, and can range in value from 0 to 1, where a Roughness value of 0 describes a particle with no useful mass available at the periphery of the particles core. Roughness is also sometimes called satellity, and is quantitative description, and is available mesoshape descriptor e.g.: in the Occhio Nano 500 instrument.

Roughness is useful in abrasive particles since the non-spherical particle herein has preferably a significant mass of material, available at the periphery of its core, as useful abrasives. This peripheral mass is useful for cleaning performance and also for preventing the particle from rolling.

Roughness is defining in 2D measurements the equivalent useful surface area outside of the core surface area of the particles ranging 0-1 whereas a Roughness of 0 describes a particle with no useful mass available at the periphery of the core particle mass. Roughness is calculated as follows:

$$Rg\gamma = (A - A(O\gamma))/A$$

Where A is the area of the particle and A(Oγ) is the surface area of what is considered the "core of the particle". A-A(Oγ) represent the "useful area at the periphery of the particle and the Roughness represent the fraction of that useful area vs. the total particle area. Oγ is called the tunable tolerance factor and is typically set at 0.8, therefore the Roughness definition is Rgγ=(A-A(0.8))/A. In order to calculate the A(0.8), the maximum amount of discs are inscribed within the particle contour at each point of the particle's edge. The size, e.g.: area of the discs inscribed is defined by the Discs' diameters whereas the diameter value ranges between 0.8×Dmax and Dmax (where Dmax is the diameter value of the biggest disc inscribed in the particle). The core area of the particle A(0.8) is defined by the area corresponding to the projection of all the inscribed discs.

Figure 3:
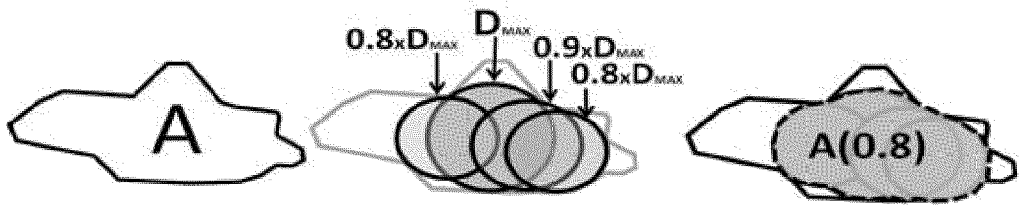
FIG. 3 is drawing showing an illustration how to calculate Roughness from the particle.

FIG. 3 is drawing showing an illustration how to calculate roughness from the particle.

The applicant has found out that the abrasive cleaning particles having a mean roughness from 0.1 to 0.3, preferably from 0.15 to 0.28 and more preferably from 0.18 to 0.25 are providing improved cleaning performance and surface safety. Mean data are extracted from volume-based vs. number-based measurements.

Thus, in a preferred embodiment of the present invention the abrasive particles herein have a mean roughness from 0.1 to 0.3 preferably from 0.15 to 0.28 and more preferably from 0.18 to 0.25.

Circularity

Circularity is a quantitative, 2-dimension image analysis shape description and is being measured according to ISO 9276-6:2008(E) section 8.2 as implemented via the Occhio Nano 500 Particle Characterisation Instrument with its accompanying software Callistro version 25 (Occhio s.a. Liege, Belgium). Circularity is a preferred mesoshape descriptor and is widely available in shape analysis instrument such as in Occhio Nano 500 or in Malvern Morphologi G3.Circularity is sometimes described in literature as being the difference between a particle's shape and a perfect sphere. Circularity values range from 0 to 1, where a circularity of 1 describes a perfectly spherical particles or disc particle as measured in a two dimensional image.

$$C = \sqrt{\frac{4\pi A}{P^2}}$$

Where A is projection area, which is 2D descriptor and P is the length of the perimeter of the particle.

The applicant has found out that the abrasive cleaning particles having mean circularity from 0.1 to 0.4, preferably from 0.15 to 0.35 and more preferably from 0.2 to 0.35 are providing improved cleaning performance and surface safety. Mean data are extracted from volume-based vs. number-based measurements.

Thus, in a preferred embodiment of the present invention the abrasive particles herein have a mean circularity from 0.1 to 0.4, preferably from 0.15 to 0.35, and more preferably from 0.2 to 0.35.

Solidity

Solidity is a quantitative, 2-dimensional image analysis shape description, and is being measured according to ISO 9276-6:2008(E) section 8.2 as implemented via the Occhio Nano 500 Particle Characterisation Instrument with its accompanying software Callistro version 25 (Occhio s.a. Liege, Belgium). The non-spherical particle herein has preferably at least one edge or surface having a concave curvature. Solidity is a mesoshape parameter, which describes the overall concavity of a particle/particle population. Solidity values range from 0 to 1, where a solidity number of 1 describes a non-concave particle, as measured in literature as being:

$$Solidity = A/Ac$$

Where A is the area of the particle and Ac is the area of the convex hull (envelope) of bounding the particle.

The applicant has found out that the abrasive cleaning particles having a mean solidity from 0.4 to 0.75, preferably solidity from 0.5 to 0.7 and more preferably from 0.55 to 0.65 are providing improved cleaning performance and surface safety. Mean data are extracted from volume-based vs. number-based measurements.

Thus, in a preferred embodiment of the present invention the abrasive particles herein have a mean solidity from 0.4 to 0.75, preferably solidity from 0.5 to 0.7, and more preferably from 0.55 to 0.65.

Solidity is sometime also named Convexity in literature or in some apparatus software using the solidity formula in place of its definition described in ISO 9276-6 (convexity=Pc/P where P is the length of the perimeter of the particle and $P_C$ is length of the perimeter of the convex hull—envelope-bounding the particle). Despite solidity and convexity being similar mesoshape descriptor in concept, the applicant refers herein to the solidity measure expressed above by the Occhio Nano 500, as indicated above.

Optionally, the particles with above defined mesoshape descriptors may be mixed with more granular/spherical type of abrasives. In that case, the applicant considers the mesoshape value range applies to the final mix.

In highly preferred embodiment the abrasive cleaning particles have a mean solidity from 0.4 to 0.75 (preferably solidity from 0.5 to 0.7, and more preferably from 0.55 to 0.65), and/or a mean circularity from 0.1 to 0.4 (preferably from 0.15 to 0.35 and more preferably from 0.2 to 0.35) and/or a mean roughness from 0.1 to 0.3 (preferably from 0.15 to 0.28 and more preferably from 0.18 to 0.25).

By the term "mean circularity", "mean solidity" or "mean roughness", the applicant consider the average of the circularity or solidity or Roughness values of each particle taken from a population of at least 10 000 particles, preferably above 50 000 particles, more preferably above 100 000 particles, after excluding from the measurement and calculation, the circularity or solidity or Roughness data of particles having area-equivalent diameter (ECD) of below 10 microns. Mean data are extracted from volume-based vs. number-based measurements.

Preferably, the non-spherical particles herein have a multitude of sharp edges. The sharp edges of the non-spherical particles are defined by edge having a tip radius below 20 μm, preferably below 8 μm, most preferably below 5 μm. The tip radius is defined by the diameter of an imaginary circle fitting the curvature of the edge extremity.

In a preferred embodiment, the abrasive cleaning particles have a mean ECD from 10 μm to 1000 μm, preferably from 50 μm to 500 μm, more preferably from 100 μm to 350 μm and most preferably from 150 to 250 μm.

Indeed, the Applicant has found that the abrasive particle size can be critical to achieve efficient cleaning performance whereas excessively abrasive population with small particle sizes e.g.: typically below 10 microns feature polishing action vs. cleaning despite featuring a high number of particles per particle load in cleaner inherent to the small particle size. On the other hand, abrasive population with excessively high particle size, e.g.: typically above 1000 micrometers, delivers not optimal cleaning efficiency since the number of particles per particle load in cleaner decreases significantly inherently to the large particle size. Additionally, excessively small particle size are not desireable in cleaner/for cleaning task since in practice, small and numerous particles are often hard to remove from the various surface topologies which requires excessive effort to remove from the user unless leaving the surface with visible particles residue. On the other hand, excessively large particle are too easily detected visually or provide bad tactile experience while handling or using the cleaner. Therefore, the applicant defines herein an optimal particle size range that deliver both optimal cleaning performance and usage experience.

The abrasive particles have size defined by their area-equivalent diameter (9276-6:2008(E) section 7) also called Equivalent Circle Diameter ECD (ASTM F1877-05 Section 11.3.2). Mean ECD of particle population is calculated as the average of respective ECD of each particles of a particle population of at least 10 000 particles, preferably above 50 000 particles, more preferably above 100 000 particles after excluding from the measurement and calculation the data of particles having area-equivalent diameter (ECD) of below 10 microns. Mean data are extracted from volume-based vs. number-based measurements.

In one preferred example, the size of the abrasive cleaning particles used in the present invention is modified during usage especially undergoing significant size reduction. Hence the particle remain visible or tactile detectable in liquid composition and at the start of the usage process to provide effective cleaning. As the cleaning process progresses, the abrasive particles disperse or break into smaller particles and become invisible to an eye or tactile undetectable.

It has surprisingly been found that the abrasive cleaning particles of the present invention show a good cleaning performance even at relatively low levels, such as preferably from 0.1% to 20% by weight of the total composition, preferably from 0.1% to 10%, more preferably from 0.5% to 5%, even more preferably from 1.0% to 3%, by weight of the total composition of said abrasive cleaning particles.

The particles used in the present invention can be white, transparent or colored by use of suitable dyes and/or pigments. Additionally suitable color stabilizing agents can be used to stabilize desired color. The abrasive particles are preferable color stable particles. By "color stable" it is meant herein that color of the particles used in the present invention will not turn yellow during storage and use.

In one preferred example, the abrasive cleaning particles used in the present invention remain visible when liquid composition is stored into a bottle while during the effective cleaning process abrasive particles disperse or break into smaller particles and become invisible to an eye.

Optional Ingredients

The compositions according to the present invention may comprise a variety of optional ingredients depending on the technical benefit aimed for and the surface treated.

Suitable optional ingredients for use herein include chelating agents, surfactants, radical scavengers, perfumes, surface-modifying polymers, solvents, builders, buffers, bactericides, hydrotropes, colorants, stabilizers, bleaches, bleach activators, suds controlling agents like fatty acids, enzymes, soil suspenders, brighteners, anti dusting agents, dispersants, pigments, and dyes.

Suspending Aid

The abrasive cleaning particles present in the composition herein are solid particles in a liquid composition. Said abrasive cleaning particles may be suspended in the liquid composition. However, it is well within the scope of the present invention that such abrasive cleaning particles are not-stably suspended within the composition and either settle or float on top of the composition. In this case, a user may have to temporally suspend the abrasive cleaning particles by agitating (e.g., shaking or stirring) the composition prior to use.

However, it is preferred herein that the abrasive cleaning particles are stably suspended in the liquid compositions herein. Thus the compositions herein comprise a suspending aid.

The suspending aid herein may either be a compound specifically chosen to provide a suspension of the abrasive cleaning particles in the liquid compositions of the present invention, such as a structurant, or a compound that also provides another function, such as a thickener or a surfactant (as described herein elsewhere).

Any suitable organic and inorganic suspending aids typically used as gelling, thickening or suspending agents in cleaning/cleansing compositions and other detergent or cosmetic compositions may be used herein. Indeed, suitable organic suspending aids include polysaccharide polymers. In addition or as an alternative, polycarboxylate polymer thickeners may be used herein. Also, in addition or as an alternative of the above, layered silicate platelets e.g.: Hectorite, bentonite or montmorillonites can also be used. Suitable commercially available layered silicates are Laponite RD® or Optigel CL® available from Rockwood Additives.

Suitable polycarboxylate polymer thickeners include (preferably lightly) crosslinked polyacrylate. A particularly suitable polycarboxylate polymer thickeners is Carbopol commercially available from Lubrizol under the trade name Carbopol 674®.

Suitable polysaccharide polymers for use herein include substituted cellulose materials like carboxymethylcellulose, ethyl cellulose, hydroxyethyl cellulose, hydroxypropyl cellulose, hydroxymethyl cellulose, succinoglycan and naturally occurring polysaccharide polymers like Xanthan gum, gellan gum, guar gum, locust bean gum, tragacanth gum, succinoglucan gum, or derivatives thereof, or mixtures thereof. Xanthan gum is commercially available from Kelco under the tradename Kelzan T.

Preferably the suspending aid herein is Xanthan gum. In an alternative embodiment, the suspending aid herein is a polycarboxylate polymer thickeners preferably a (preferably lightly) crosslinked polyacrylate. In a highly preferred embodiment herein, the liquid compositions comprise a combination of a polysaccharide polymer or a mixture thereof, preferably Xanthan gum, with a polycarboxylate polymer or a mixture thereof, preferably a crosslinked polyacrylate.

As a preferred example, Xanthan gum is preferably present at levels between 0.1% to 5% by weight of the total composition, more preferably from 0.5% to 2%, even more preferably from 0.8% to 1.2%.

Organic Solvent

As an optional but highly preferred ingredient the composition herein comprises an organic solvents or mixtures thereof.

The compositions herein comprise from 0% to 30% by weight of the total composition of an organic solvent or a mixture thereof, more preferably 1.0% to 20% and most preferably, 2% to 15%.

Suitable solvents can be selected from the group consisting of: aliphatic alcohols, ethers and diethers having from 4 to 14 carbon atoms, preferably from 6 to 12 carbon atoms, and more preferably from 8 to 10 carbon atoms; glycols or alkoxylated glycols; glycol ethers; alkoxylated aromatic alcohols; aromatic alcohols; terpenes; and mixtures thereof. Aliphatic alcohols and glycol ether solvents are most preferred.

Aliphatic alcohols, of the formula R—OH wherein R is a linear or branched, saturated or unsaturated alkyl group of from 1 to 20 carbon atoms, preferably from 2 to 15 and more preferably from 5 to 12, are suitable solvents. Suitable aliphatic alcohols are methanol, ethanol, propanol, isopropanol or mixtures thereof. Among aliphatic alcohols, ethanol and isopropanol are most preferred because of their high vapour pressure and tendency to leave no residue.

Suitable glycols to be used herein are according to the formula HO—$CR_1R_2$—OH wherein R1 and R2 are independently H or a $C_2$-$C_{10}$ saturated or unsaturated aliphatic hydrocarbon chain and/or cyclic. Suitable glycols to be used herein are dodecaneglycol and/or propanediol.

In one preferred embodiment, at least one glycol ether solvent is incorporated in the compositions of the present invention. Particularly preferred glycol ethers have a terminal $C_3$-$C_6$ hydrocarbon attached to from one to three ethylene glycol or propylene glycol moieties to provide the appropriate degree of hydrophobicity and, preferably, surface activity. Examples of commercially available solvents based on ethylene glycol chemistry include mono-ethylene glycol n-hexyl ether (Hexyl Cellosolve®) available from Dow Chemical. Examples of commercially available solvents based on propylene glycol chemistry include the di-, and tri-propylene glycol derivatives of propyl and butyl alcohol, which are available from Arco under the trade names Arcosolv® and Dowanol®.

In the context of the present invention, preferred solvents are selected from the group consisting of mono-propylene glycol mono-propyl ether, di-propylene glycol mono-propyl ether, mono-propylene glycol mono-butyl ether, di-propylene glycol mono-propyl ether, di-propylene glycol mono-butyl ether; tri-propylene glycol mono-butyl ether; ethylene glycol mono-butyl ether; di-ethylene glycol mono-butyl ether, ethylene glycol mono-hexyl ether and di-ethylene glycol mono-hexyl ether, and mixtures thereof. "Butyl" includes normal butyl, isobutyl and tertiary butyl groups. Mono-propylene glycol and mono-propylene glycol mono-butyl ether are the most preferred cleaning solvent and are available under the tradenames Dowanol DPnP® and Dowanol DPnB®. Di-propylene glycol mono-t-butyl ether is commercially available from Arco Chemical under the tradename Arcosolv PTB®.

In a particularly preferred embodiment, the cleaning solvent is purified so as to minimize impurities. Such impurities include aldehydes, dimers, trimers, oligomers and other by-products. These have been found to deleteriously affect product odour, perfume solubility and end result. The inventors have also found that common commercial solvents, which contain low levels of aldehydes, can cause irreversible and irreparable yellowing of certain surfaces. By purifying the cleaning solvents so as to minimize or eliminate such impurities, surface damage is attenuated or eliminated.

Though not preferred, terpenes can be used in the present invention. Suitable terpenes to be used herein monocyclic terpenes, dicyclic terpenes and/or acyclic terpenes. Suitable terpenes are: D-limonene; pinene; pine oil; terpinene; terpene derivatives as menthol, terpineol, geraniol, thymol; and the citronella or citronellol types of ingredients.

Suitable alkoxylated aromatic alcohols to be used herein are according to the formula R-$(A)_n$-OH wherein R is an alkyl substituted or non-alkyl substituted aryl group of from 1 to 20 carbon atoms, preferably from 2 to 15 and more preferably from 2 to 10, wherein A is an alkoxy group preferably butoxy, propoxy and/or ethoxy, and n is an integer of from 1 to 5, preferably 1 to 2. Suitable alkoxylated aromatic alcohols are benzoxyethanol and/or benzoxypropanol.

Suitable aromatic alcohols to be used herein are according to the formula R—OH wherein R is an alkyl substituted or non-alkyl substituted aryl group of from 1 to 20 carbon atoms, preferably from 1 to 15 and more preferably from 1 to 10. For example a suitable aromatic alcohol to be used herein is benzyl alcohol.

Surfactants

The compositions herein may comprise a nonionic, anionic, zwitterionic, cationic and amphoteric surfactant or mixtures thereof. Suitable surfactants are those selected from the group consisting of nonionic, anionic, zwitterionic, cationic and amphoteric surfactants, having hydrophobic chains containing from 8 to 18 carbon atoms. Examples of suitable surfactants are described in McCutcheon's Vol. 1: Emulsifiers and Detergents, North American Ed., McCutcheon Division, MC Publishing Co., 2002.

Preferably, the composition herein comprises from 0.01% to 20% by weight of the total composition of a surfactant or a mixture thereof, more preferably from 0.5% to 10%, and most preferably from 1% to 5%.

Non-ionic surfactants are highly preferred for use in the compositions of the present invention. Non-limiting examples of suitable non-ionic surfactants include alcohol alkoxylates, alkyl polysaccharides, amine oxides, block copolymers of ethylene oxide and propylene oxide, fluoro surfactants and silicon based surfactants. Preferably, the aqueous compositions comprise from 0.01% to 20% by weight of the total composition of a non-ionic surfactant or a mixture thereof, more preferably from 0.5% to 10%, and most preferably from 1% to 5%.

A preferred class of non-ionic surfactants suitable for the present invention is alkyl ethoxylates. The alkyl ethoxylates of the present invention are either linear or branched, and contain from 8 carbon atoms to 16 carbon atoms in the hydrophobic tail, and from 3 ethylene oxide units to 25 ethylene oxide units in the hydrophilic head group. Examples of alkyl ethoxylates include Neodol 91-6°, Neodol 91-8® supplied by the Shell Corporation (P.O. Box 2463, 1 Shell Plaza, Houston, Tex.), and Alfonic 810-60® supplied by Condea Corporation, (900 Threadneedle P.O. Box 19029, Houston, Tex.). More preferred alkyl ethoxylates comprise from 9 to 12 carbon atoms in the hydrophobic tail, and from 4 to 9 oxide units in the hydrophilic head group. A most preferred alkyl ethoxylate is $C_{9-11}$ $EO_5$, available from the Shell Chemical Company under the tradename Neodol 91-5®. Non-ionic ethoxylates can also be derived from branched alcohols. For example, alcohols can be made from branched olefin feedstocks such as propylene or butylene. In a preferred embodiment, the branched alcohol is either a 2-propyl-1-heptyl alcohol or 2-butyl-1-octyl alcohol. A desirable branched alcohol ethoxylate is 2-propyl-1-heptyl EO7/AO7, manufactured and sold by BASF Corporation under the tradename Lutensol XP 79/XL 79®.

Another class of non-ionic surfactant suitable for the present invention is alkyl polysaccharides. Such surfactants are disclosed in U.S. Pat. Nos. 4,565,647, 5,776,872, 5,883,062, and 5,906,973. Among alkyl polysaccharides, alkyl polyglycosides comprising five and/or six carbon sugar rings are preferred, those comprising six carbon sugar rings are more preferred, and those wherein the six carbon sugar ring is derived from glucose, i.e., alkyl polyglucosides ("APG"), are most preferred. The alkyl substituent in the APG chain length is preferably a saturated or unsaturated alkyl moiety containing from 8 to 16 carbon atoms, with an average chain length of 10 carbon atoms. $C_8$-$C_{16}$ alkyl polyglucosides are commercially available from several suppliers (e.g., Simusol® surfactants from Seppic Corporation, 75 Quai d'Orsay, 75321 Paris, Cedex 7, France, and Glucopon 220®, Glucopon 225®, Glucopon 425®, Plantaren 2000 N®, and Plantaren 2000 N UP®, from Cognis Corporation, Postfach 13 01 64, D 40551, Dusseldorf, Germany).

Another class of non-ionic surfactant suitable for the present invention is amine oxide. Amine oxides, particularly those comprising from 10 carbon atoms to 16 carbon atoms in the hydrophobic tail, are beneficial because of their strong cleaning profile and effectiveness even at levels below 0.10%. Additionally $C_{10-16}$ amine oxides, especially $C_{12}$-$C_{14}$ amine oxides are excellent solubilizers of perfume. Alternative non-ionic detergent surfactants for use herein are alkoxylated alcohols generally comprising from 8 to 16 carbon atoms in the hydrophobic alkyl chain of the alcohol. Typical alkoxylation groups are propoxy groups or ethoxy groups in combination with propoxy groups, yielding alkyl ethoxy propoxylates. Such compounds are commercially available under the tradename Antarox® available from Rhodia (40 Rue de la Haie-Coq F-93306, Aubervilliers Cédex, France) and under the tradename Nonidet® available from Shell Chemical.

The condensation products of ethylene oxide with a hydrophobic base formed by the condensation of propylene oxide with propylene glycol are also suitable for use herein. The hydrophobic portion of these compounds will preferably have a molecular weight of from 1500 to 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to 40 moles of ethylene oxide. Examples of compounds of this type include certain of the commercially available Pluronic® surfactants, marketed by BASF. Chemically, such surfactants have the structure $(EO)_x(PO)_y(EO)_z$ or $(PO)_x(EO)_y(PO)_z$ wherein x, y, and z are from 1 to 100, preferably 3 to 50. Pluronic® surfactants known to be good wetting surfactants are more preferred. A description of the Pluronic® surfactants, and properties thereof, including wetting properties, can be found in the brochure entitled "BASF Performance Chemicals Plutonic® & Tetronic® Surfactants", available from BASF.

Other suitable though not preferred non-ionic surfactants include the polyethylene oxide condensates of alkyl phenols, e.g., the condensation products of alkyl phenols having an alkyl group containing from 6 to 12 carbon atoms in either a straight chain or branched chain configuration, with ethylene oxide, the said ethylene oxide being present in amounts equal to 5 to 25 moles of ethylene oxide perf mole of alkyl phenol. The alkyl substituent in such compounds can be derived from oligomerized propylene, diisobutylene, or from other sources of iso-octane n-octane, iso-nonane or n-nonane. Other non-ionic surfactants that can be used include those derived from natural sources such as sugars and include $C_8$-$C_{16}$ N-alkyl glucose amide surfactants.

Suitable anionic surfactants for use herein are all those commonly known by those skilled in the art. Preferably, the anionic surfactants for use herein include alkyl sulphonates, alkyl aryl sulphonates, alkyl sulphates, alkyl alkoxylated sulphates, $C_6$-$C_{20}$ alkyl alkoxylated linear or branched diphenyl oxide disulphonates, or mixtures thereof.

Suitable alkyl sulphonates for use herein include water-soluble salts or acids of the formula $RSO_3M$ wherein R is a $C_6$-$C_{20}$ linear or branched, saturated or unsaturated alkyl group, preferably a $C_8$-C18 alkyl group and more preferably a $C_{10}$-$C_{16}$ alkyl group, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like).

Suitable alkyl aryl sulphonates for use herein include water-soluble salts or acids of the formula $RSO_3M$ wherein R is an aryl, preferably a benzyl, substituted by a $C_6$-$C_{20}$ linear or branched saturated or unsaturated alkyl group, preferably a $C_8$-$C_{18}$ alkyl group and more preferably a $C_{10}$-$C_{16}$ alkyl group, and M is H or a cation, e.g., an alkali metal cation (e.g., sodium, potassium, lithium, calcium, magnesium and the like) or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like).

An example of a $C_{14}$-$C_{16}$ alkyl sulphonate is Hostapur® SAS available from Hoechst. An example of commercially available alkyl aryl sulphonate is Lauryl aryl sulphonate from Su.Ma. Particularly preferred alkyl aryl sulphonates are alkyl benzene sulphonates commercially available under trade name Nansa® available from Albright & Wilson.

Suitable alkyl sulphate surfactants for use herein are according to the formula $R_1SO_4M$ wherein $R_1$ represents a hydrocarbon group selected from the group consisting of straight or branched alkyl radicals containing from 6 to 20 carbon atoms and alkyl phenyl radicals containing from 6 to 18 carbon atoms in the alkyl group. M is H or a cation, e.g., an alkali metal cation (e.g., sodium, potassium, lithium, calcium, magnesium and the like) or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like). Particularly preferred branched alkyl sulphates to be used herein are those containing from 10 to 14 total carbon atoms like Isalchem 123 AS®. Isalchem 123 AS® commercially available from Enichem is a $C_{12\cdot13}$ surfactant which is 94% branched. This material can be described as $CH_3—(CH_2)_m—CH(CH_2OSO_3Na)—(CH_2)_n—CH_3$ where n+m=8-9. Also preferred alkyl sulphates are the alkyl sulphates where the alkyl chain comprises a total of 12 carbon atoms, i.e., sodium 2-butyl octyl sulphate. Such alkyl sulphate is commercially available from Condea under the trade name Isofol® 12S. Particularly suitable liner alkyl sulphonates include $C_{12}$-$C_{16}$ paraffin sulphonate like Hostapur® SAS commercially available from Hoechst.

Suitable alkyl alkoxylated sulphate surfactants for use herein are according to the formula $RO(A)_mSO_3M$ wherein R is an unsubstituted $C_6$-$C_{20}$ alkyl or hydroxyalkyl group having a $C_6$-$C_{20}$ alkyl component, preferably a $C_{12}$-$C_{20}$ alkyl or hydroxyalkyl, more preferably $C_{12}$-$C_{18}$ alkyl or hydroxyalkyl, A is an ethoxy or propoxy unit, m is greater than zero, typically between 0.5 and 6, more preferably between 0.5 and 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperdinium and cations derived from alkanolamines such as ethylamine, diethylamine, triethylamine, mixtures thereof, and the like. Exemplary surfactants are $C_{12}$-$C_{18}$ alkyl polyethoxylate (1.0) sulfate ($C_{12}$-$C_{18}$E(1.0)SM), $C_{12}$-$C_{18}$ alkyl polyethoxylate (2.25) sulfate ($C_{12}$-$C_{18}$E(2.25)SM), $C$-$_{12}$-$C_{18}$ alkyl polyethoxylate (3.0) sulfate ($C_{12}$-$C_{18}$E(3.0)SM), $C_{12}$-$C_{18}$ alkyl polyethoxylate (4.0) sulfate ($C_{12}$-$C_{18}$E (4.0)SM), wherein M is conveniently selected from sodium and potassium.

Suitable $C_6$-$C_{20}$ alkyl alkoxylated linear or branched diphenyl oxide disulphonate surfactants for use herein are according to the following formula:

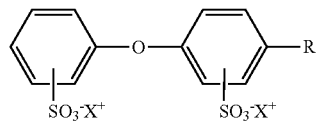

wherein R is a $C_6$-$C_{20}$ linear or branched, saturated or unsaturated alkyl group, preferably a $C_{12}$-$C_{18}$ alkyl group and more preferably a $C_{14}$-$C_{16}$ alkyl group, and X+ is H or a cation, e.g., an alkali metal cation (e.g., sodium, potassium, lithium, calcium, magnesium and the like). Particularly suitable $C_6$-$C_{20}$ alkyl alkoxylated linear or branched diphenyl oxide disulphonate surfactants to be used herein are the $C_{12}$ branched di phenyl oxide disulphonic acid and $C_{16}$ linear di phenyl oxide disulphonate sodium salt respectively commercially available by DOW under the trade name Dowfax 2A1® and Dowfax 8390®.

Other anionic surfactants useful herein include salts (including, for example, sodium, potassium, ammonium, and substituted ammonium salts such as mono-, di- and triethanolamine salts) of soap, $C_8$-$C_{24}$ olefinsulfonates, sulphonated polycarboxylic acids prepared by sulphonation of the pyrolyzed product of alkaline earth metal citrates, e.g., as described in British patent specification No. U.S. Pat. No. 1,082,179, $C_8$-$C_{24}$ alkylpolyglycolethersulfates (containing up to 10 moles of ethylene oxide); alkyl ester sulfonates such as $C_{14}$-$C_{16}$ methyl ester sulfonates; acyl glycerol sulfonates, fatty oleyl glycerol sulfates, alkyl phenol ethylene oxide ether sulfates, alkyl phosphates, isethionates such as the acyl isethionates, N-acyl taurates, alkyl succinamates and sulfosuccinates, monoesters of sulfosuccinate (especially saturated and unsaturated $C_{12}$-$C_{18}$ monoesters) diesters of sulfosuccinate (especially saturated and unsaturated $C_6$-$C_{14}$ diesters), acyl sarcosinates, sulfates of alkylpolysaccharides such as the sulfates of alkylpolyglucoside (the nonionic nonsulfated compounds being described below), alkyl polyethoxy carboxylates such as those of the formula $RO(CH_2CH_2O)_k$ $CH_2COO^-M^+$ wherein R is a $C_8$-$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

Zwitterionic surfactants represent another class of preferred surfactants within the context of the present invention.

Zwitterionic surfactants contain both cationic and anionic groups on the same molecule over a wide pH range. The typical cationic group is a quaternary ammonium group, although other positively charged groups like sulfonium and phosphonium groups can also be used. The typical anionic groups are carboxylates and sulfonates, preferably sulfonates, although other groups like sulfates, phosphates and the like, can be used. Some common examples of these detergents are described in the patent literature: U.S. Pat. Nos. 2,082,275, 2,702,279 and 2,255,082.

A specific example of a zwitterionic surfactant is 3-(N-dodecyl-N,N-dimethyl)-2-hydroxypropane-1-sulfonate (Lauryl hydroxyl sultaine) available from the McIntyre Company (24601 Governors Highway, University Park, Ill. 60466, USA) under the tradename Mackam LHS®. Another specific zwitterionic surfactant is $C_{12\text{-}14}$ acylamidopropylene (hydroxypropylene) sulfobetaine that is available from McIntyre under the tradename Mackam 50-SB®. Other very useful zwitterionic surfactants include hydrocarbyl, e.g., fatty alkylene betaines. A highly preferred zwitterionic surfactant is Empigen BB®, a coco dimethyl betaine produced by Albright & Wilson. Another equally preferred zwitterionic surfactant is Mackam 35HP®, a coco amido propyl betaine produced by McIntyre.

Another class of preferred surfactants comprises the group consisting of amphoteric surfactants. One suitable amphoteric surfactant is a $C_8$-$C_{16}$ amido alkylene glycinate surfactant ('ampho glycinate'). Another suitable amphoteric surfactant is a $C_8$-$C_{16}$ amido alkylene propionate surfactant ('ampho propionate'). Other suitable, amphoteric surfactants are represented by surfactants such as dodecylbeta-alanine, N-alkyltaurines such as the one prepared by reacting dodecylamine with sodium isethionate according to the teaching of U.S. Pat. No. 2,658,072, N-higher alkylaspartic acids such as those produced according to the teaching of U.S. Pat. No. 2,438,091, and the products sold under the trade name "Miranol®", and described in U.S. Pat. No. 2,528,378.

Chelating Agents

One class of optional compounds for use herein includes chelating agents or mixtures thereof. Chelating agents can be incorporated in the compositions herein in amounts ranging from 0.0% to 10.0% by weight of the total composition, preferably 0.01% to 5.0%.

Suitable phosphonate chelating agents for use herein may include alkali metal ethane 1-hydroxy diphosphonates (HEDP), alkylene poly (alkylene phosphonate), as well as amino phosphonate compounds, including amino aminotri (methylene phosphonic acid) (ATMP), nitrilo trimethylene phosphonates (NTP), ethylene diamine tetra methylene phosphonates, and diethylene triamine penta methylene phosphonates (DTPMP). The phosphonate compounds may be present either in their acid form or as salts of different cations on some or all of their acid functionalities. Preferred phosphonate chelating agents to be used herein are diethylene triamine penta methylene phosphonate (DTPMP) and ethane 1-hydroxy diphosphonate (HEDP). Such phosphonate chelating agents are commercially available from Monsanto under the trade name DEQUEST®.

Polyfunctionally-substituted aromatic chelating agents may also be useful in the compositions herein. See U.S. Pat. No. 3,812,044, issued May 21, 1974, to Connor et al. Preferred compounds of this type in acid form are dihydroxydisulfobenzenes such as 1,2-dihydroxy -3,5-disulfobenzene.

A preferred biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987, to Hartman and Perkins. Ethylenediamine N,N'- disuccinic acids is, for instance, commercially available under the tradename ssEDDS® from Palmer Research Laboratories.

Suitable amino carboxylates for use herein include ethylene diamine tetra acetates, diethylene triamine pentaacetates, diethylene triamine pentaacetate (DTPA),N- hydroxyethylethylenediamine tri acetates, nitrilotri-acetates, ethylenediamine tetrapropionates, triethylenetetraaminehexa-acetates, ethanol-diglycines, propylene diamine tetracetic acid (PDTA) and methyl glycine di-acetic acid (MGDA), both in their acid form, or in their alkali metal, ammonium, and substituted ammonium salt forms. Particularly suitable amino carboxylates to be used herein are diethylene triamine penta acetic acid, propylene diamine tetracetic acid (PDTA) which is, for instance, commercially available from BASF under the trade name Trilon FS® and methyl glycine di-acetic acid (MGDA).

Further carboxylate chelating agents for use herein include salicylic acid, aspartic acid, glutamic acid, glycine, malonic acid or mixtures thereof.

Radical Scavenger

The compositions of the present invention may further comprise a radical scavenger or a mixture thereof.

Suitable radical scavengers for use herein include the well-known substituted mono and dihydroxy benzenes and their analogs, alkyl and aryl carboxylates and mixtures thereof. Preferred such radical scavengers for use herein include di-tert-butyl hydroxy toluene (BHT), hydroquinone, di-tert-butyl hydroquinone, mono-tert-butyl hydroquinone, tert-butylhydroxy anysole, benzoic acid, toluic acid, catechol, t-butyl catechol, benzylamine, 1,1,3-tris(2-methyl-4-hydroxy-5-t-butylphenyl)butane, n-propyl-gallate or mixtures thereof and highly preferred is di-tert-butyl hydroxy toluene. Such radical scavengers like N-propyl-gallate may be commercially available from Nipa Laboratories under the trade name Nipanox S1®.

Radical scavengers, when used, may be typically present herein in amounts up to 10% by weight of the total composition and preferably from 0.001% to 0.5%. The presence of radical scavengers may contribute to the chemical stability of the compositions of the present invention.

Perfume

Suitable perfume compounds and compositions for use herein are for example those described in EP-A-0 957 156 under the paragraph entitled "Perfume", on page 13.The compositions herein may comprise a perfume ingredient, or mixtures thereof, in amounts up to 5.0% by weight of the total composition, preferably in amounts of 0.1% to 1.5%.

Dye

The liquid compositions according to the present invention may be coloured. Accordingly, they may comprise a dye or a mixture thereof.

Delivery Form of the Compositions

The compositions herein may be packaged in a variety of suitable packaging known to those skilled in the art, such as plastic bottles for pouring liquid compositions, squeeze bottles or bottles equipped with a trigger sprayer for spraying liquid compositions. Alternatively, the paste-like compositions according to the present invention may by packaged in a tube.

In an alternative embodiment herein, the liquid composition herein is impregnated onto a substrate, preferably the substrate is in the form of a flexible, thin sheet or a block of material, such as a sponge.

Suitable substrates are woven or non-woven sheets, cellulosic material based sheets, sponge or foam with open cell structures e.g.: polyurethane foams, cellulosic foam, melamine foam, etc.

The Process of Cleaning a Surface

The present invention encompasses a process of cleaning and/or cleansing a surface with a liquid composition according to the present invention. Suitable surfaces herein are described herein above under the heading "The liquid cleaning/cleansing composition".

In a preferred embodiment said surface is contacted with the composition according to the present invention, preferably wherein said composition is applied onto said surface.

In another preferred embodiment, the process herein comprises the steps of dispensing (e.g., by spraying, pouring, squeezing) the liquid composition according to the present invention from a container containing said liquid composition and thereafter cleaning and/or cleansing said surface. The composition herein may be in its neat form or in its diluted form.

By "in its neat form", it is to be understood that said liquid composition is applied directly onto the surface to be treated without undergoing any dilution, i.e., the liquid composition herein is applied onto the surface as described herein.

By "diluted form", it is meant herein that said liquid composition is diluted by the user typically with water. The liquid composition is diluted prior to use to a typical dilution level of up to 10 times its weight of water. A usually recommended dilution level is a 10% dilution of the composition in water.

The composition herein may be applied using an appropriate implement, such as a mop, paper towel, brush (e.g., a toothbrush) or a cloth, soaked in the diluted or neat composition herein. Furthermore, once applied onto said surface said composition may be agitated over said surface using an appropriate implement. Indeed, said surface may be wiped using a mop, paper towel, brush or a cloth.

The process herein may additionally contain a rinsing step, preferably after the application of said composition. By "rinsing", it is meant herein contacting the surface cleaned/cleansed with the process according to the present invention with substantial quantities of appropriate solvent, typically water, directly after the step of applying the liquid composition herein onto said surface. By "substantial quantities", it is meant herein between 0.01 lt. and 1 lt. of water per $m^2$ of surface, more preferably between 0.1 lt. and 1 lt. of water per $m^2$ of surface.

In a preferred embodiment herein, process of cleaning is a process of cleaning household hard surfaces with a liquid composition according to present invention.

Cleaning Effectiveness

Cleaning Effectiveness test method:

The tiles (typically glossy, white, ceramic 24 cm×4 cm) are covered with 0.3 g of typical greasy soap scum soils mainly based on calcium stearate and artificial body soils commercially available (applied to the tile via a sprayer). The soiled tiles are then dried in an oven at a temperature of 140° C. for 10-45 minutes, preferably 40 minutes and then aged between 2 and 12 hours at room temperature (around 20° C.) in a controlled environment humidity (60-85% RH, preferably 75% RH). Then the soiled tiles are cleaned using 5 ml of the composition of the present invention poured directly on a Spontex® cellulose sponge pre-wetted with water. The sponge is then mounted on a Wet Abrasion Scrub Tester Instrument (such as made by Sheen Instruments Ltd. Kingston, England) with the particle composition coated side facing the tile. The abrasion tester can be configured to supply pressure (e.g. 600 g), and move the sponge over the test surface with a set stroke length (e.g. 30 cm), at set speed (e.g. 37 strokes per minute). The ability of the composition to remove greasy soap scum is measured through the number of strokes needed to perfectly clean the surface, as determined by visual assessment. The lower the number of strokes, the higher the greasy soap scum cleaning ability of the composition.

Cleaning data below are achieved with 1% of Abrasive particles in cleaner. Note Abrasive particles used to generate the example cleaning data were made from polyurethane foam having a MOHS hardness value of 2.

Impact of foam structure: Foam is made of polyurethane rigid foam of Vickers hardness value of 7.

Cleaning data made with 1% particle in cleaning composition.

| Sample # | Particles Size selection (via air sieving) | Particle shape parameter: Circulatity, Solidity, Roughness | Foam density | Foam cell size | Foam L/T ratio | # strokes to clean Greasy soap scum |
|---|---|---|---|---|---|---|
| 0 | No particles | — | — | — | — | >100 (no clean) |
| 1 | 355-250 μm | C: 0.19; S: 0.59; R: 0.24 | 33 kg/m3 | 420 μm | 5 | 21 |
| 2 | 355-250 μm | C: 0.23; S: 0.66; R: 0.19 | 60 kg/m3 | 270 μm | 4 | 19 |
| 3 | 355-250 μm | C: 0.33; S: 0.77; R: 0.15 | 120 kg/m3 | 200 μm | 2.2 | 33 |
| 4 | 355-250 μm | C: 0.42; S: 0.82; R: 0.11 | 320 kg/m3 | 180 μm | 1.5 | 70 |

Impact of foam structure Foam is made of polyurethane rigid foam of Vickers hardness value of 7. Cleaning data made with 1% particle in cleaner.

| Sample # | Particles Size selection (via air sieving) | Particle shape parameter: Circulatity, Solidity, Roughness | Foam density | Foam cell size | % closed cell | Cleaning index to clean Greasy soap scum |
|---|---|---|---|---|---|---|
| 0 | — | — | — | — | — | <20% (no clean) |
| 1 | 355-250 μm | C: 0.19; S: 0.59; R: 0.24 | 33 kg/m3 | 420 μm | 5 | Ref. (100%) |
| 5 | 355-250 μm | C: 0.23; S: 0.67; R0.18 | 36 kg/m3 | 506 μm | 66 | 98% |
| 6 | 355-250 μm | C: 0.25; S: 0.7; R: 0.18 | 59 kg/m3 | 391 μm | 1 | 96% |
| 7 | 355-250 μm | C: 0.19; S0.65; R: 0.21 | 36 kg/m3 | 406 μm | 84 | 94% |
| 8 | 355-250 μm | C: 0.18; S: 0.65; R: 0.22 | 35 kg/m3 | 431 μm | 84 | 83% |
| 9 | 355-250 μm | C: 0.34; S: 0.76; R: 0.12 | 62 kg/m3 | 765 μm | 0 | 81% |
| 10 | 355-250 μm | C: 0.23; S: 0.71; R: 0.19 | 53 kg/m3 | 468 μm | 84 | 80% |
| 11 | 355-250 μm | C: 0.24; S: 0.71; R: 0.16 | 54 kg/m3 | 413 μm | 81 | 72% |
| 12 | 355-250 μm | C: 0.49; S: 0.83; R: 0.07 | 61 kg/m3 | 1304 μm | 71 | 58% |
| 13 | 355-250 μm | C: 0.45; S: 0.82; R: 0.08 | 60 kg/m3 | 1291 μm | 62 | 51% |
| 14 | 355-250 μm | C: 0.51; S: 0.86; R: 0.06 | 65 kg/m3 | 2228 μm | 49 | 48% |

Impact of foam structure: Foam is made of polyurethane rigid foam of Vickers hardness value of 7. Cleaning data made with 1% particle in cleaning composition.

| Sample # | Particles Size selection (via air sieving) | Foam density | Foam cell size | Foam L/T ratio | % closed cell | Cleaning index to clean Greasy soap scum |
|---|---|---|---|---|---|---|
| 15 | 355-250 μm | 43 kg/m3 | 250 μm | 5.7 | 27% | Ref. (100%) |
| 16 | 355-250 μm | 55 kg/m3 | 310 μm | 5 | 18% | 106.5% |
| 17 | 355-250 μm | 44 kg/m3 | 380 μm | 5.9 | 5% | 109% |
| 18 | 355-250 μm | 44 kg/m3 | 350 μm | 5.6 | 5% | 117% |

Impact of over grinding: : Foam is made of polyurethane rigid foam of Vickers hardness value of 7, density 33 Kg/m3, average L/T ratio 5, average foam cell size 420 μm (note : incidentally, particle target size >210 μm). Cleaning data made with 1% particle in cleaning composition.

| Sample # | Particle Size selection (via air sieving) | Particle shape parameter: Circularity, Solidity, Roughness | Foam density | Foam cell size | Foam L/T ratio | # strokes to clean Greasy soap scum |
|---|---|---|---|---|---|---|
| 1 (tris) | 125-20 μm | C: 0.31; S: 0.67; R: 0.11 | 33 kg/m3 | 420 μm | 5 | 49 |
| 1 (bis) | 250-125 μm | C: 0.22; S: 0.56; R: 0.21 | 33 kg/m3 | 420 μm | 5 | 26 |
| 1 | 355-250 μm | C: 0.19; S: 0.59; R: 0.24 | 33 kg/m3 | 420 μm | 5 | 21 |

Surface Safety
Surface Damage Method:

To measure the surface damage produced by the test particles, mix 0.2 g of the abrasive particles to be tested, with 4 g of an aqueous lotion of NEODOL C9-11 EO8 surfactant (Shell Chemicals) (3% surfactant by weight). Wet a new cellulose kitchen sponge (such as Spontex®) of dimensions 4 cm×8.5 cm (and 4.5 cm thick) with 24 ml of distilled or deionised water, then load by uniformly distributing the surfactant and particle mixture over one 4 cm×8.5 cm side of the sponge. The sponge is then mounted on a Wet Abrasion Scrub Tester Instrument (such as made by Sheen Instruments. Ltd, Kingston, England) with the particle and surfactant coated side facing the test surface. The test surface to be used should be a new sheet of uncolored, transparent, virgin Poly(methyl methacrylate) (also known as PMMA, Plexiglass, Perspex, Lucite), having a Vickers HV Hardness Value of 25 kg/square mm (+/−2) (as measured using standard test method ISO 14577). The abrasion tester should be configured to supply 600 g of pressure and move the sponge over the test surface with a stroke length of 30 cm, at a speed of 37 strokes per minute. The wet abrasion scrub tester is should be allowed to execute 1,000 strokes (i.e.: 1,000 single-direction displacements), then the sponge is re-loaded with an additional 0.2 g of abrasive and 4 g of surfactant lotion. No additional water should be applied when re-loading the sponge. The sponge is to be reloaded in this manner every 1,000 strokes, for ten consecutive loadings (i.e., 10,000 strokes in total per test surface). Assessment of damage to the test surface is conducted after 10,000 strokes have been completed. The sponge should not be replaced during the test unless it becomes damaged such as torn or ripped. In which case a new sponge should be wetted, loaded and installed as per instructions for the original sponge, in order to complete the test.

To assess surface damage on the Poly(methyl methacrylate) test surface, visual grading is conducted according to the following 5-level surface damage grading scale: 0=I see no scratches; 1=I think I see scratches; 2=I definitely see small scratches; 3=I see lots of scratches; 4=I see a lot of damage. The Visual Damage Grade is the average of the grades given by 5 independent graders.

Additionally, the surface damage on the Poly(methyl methacrylate) test surface is also assessed by measuring Roughness of the sponge-abraded surface, using a Roughness Tester such as the TR 200 (PortableTesters.com LLC). Several profile roughness parameters are measured, including: average maximum height (Rz);total peak-to-valley height (Rt); Maximum peak height (Rp); maximum valley depth (Rv); mean spacing of irregularities (RSm); and skewness (Rsk).

| Surface damage assessment | No particle | Shape particles* | UN-shaped particles* |
|---|---|---|---|
| Sample# | NA | 1 (bis) | 3 (bis) |
| Size selection (via air sieving) | NA | 250-125 μm | 250-125 μm |
| Particle shape parameter: Circularity, Solidity, Roughness | NA | C: 0.22; S: 0.56; R: 0.21 | C: 0.47; S: 0.82; R: 0.08 |
| Foam density | NA | 33 kg/m3 | 320 kg/m3 |
| Foam cell size | NA | 420 μm | 180 μm |
| Foam L/T ratio | NA | 5 | 1.5 |
| Visual damage grade | 0 | 0.4 | 2.7 |
| Roughness parameter: Rz (Average maximum Height of profile) | 0.079 μm | 0.130 μm | 0.271 μm |
| Roughness parameter: Rt (total peak-to-valley height) | 0.186 μm | 0.413 μm | 0.906 μm |

| Surface damage assessment | No particle | Shape particles* | UN-shaped particles* |
|---|---|---|---|
| Roughness parameter: Rp (Maximum Profile Peak Height) | 0.061 μm | 0.091 μm | 0.154 μm |
| Roughness parameter: Rv (Maximum Profile Valley Depth) | 0.019 μm | 0.040 μm | 0.117 μm |
| Roughness parameter: RSm (Mean Spacing of Profile Irregularities) | 7.0833 mm | 4.3055 mm | 2.2685 mm |
| Roughness parameter: Rsk (Skewness of profil) | 2.839 | 3.065 | 4.5 |

*Note Abrasive particle made from polyurethane foam of Vickers hardness value of 7.

EXAMPLES

These following compositions were made comprising the listed ingredients in the listed proportions (weight %). Examples 1-43 herein are met to exemplify the present invention, but are not necessarily used to limit or otherwise define the scope of the present invention.

Abrasive particle used in the examples below were ground from rigid polyurethane foam (controlled foam structure e.g.: foam density, cell size, strut aspect ratio and % cell size content). Polyurethane foam is synthesized from reaction of a diisocyanate (e.g.: base on polymeric methylene diphenyl diisocyanate) and polyols (e.g.: polyether or polyester-based polyol). Wherein the diisocyanate is for example Lupranate M200R from BASF and the polyol is for example Lupranol 3423 from BASF. Foam were ground into small particles and sieved using a rotary mill and particle selection was done with used of air jet sieving instrument from Retsch.

| Hard surface cleaner Bathroom composition: | | | |
|---|---|---|---|
| % Weight | 1 | 2 | 3 |
| C9-C11 EO8 (Neodol 91-8 ®) | 3 | 2.5 | 3.5 |
| Alkyl Benzene sulfonate | | 1 | |
| C12-14-dimethyl Aminoxide | | 1 | |
| n-Butoxy Propoxy Propanol | | 2 | 2.5 |
| Hydrogene Peroxide | 3 | | |
| Hydrophobic ethoxylated polyurethane (Acusol 882 ®) | 1.5 | 1 | 0.8 |
| Lactic Acid | 3 | | 3.5 |
| Citric Acid | | 3 | 0.5 |
| Polysaccharide (Xanthan Gum, Keltrol CG-SFT ® Kelco) | 0.25 | 0.25 | 0.25 |
| Perfume | 0.35 | 0.35 | 0.35 |
| Abrasive particles made from polyurethane foam: samples # 1 | 1 | 1 | 1 |
| Water | Balance | Balance | Balance |
| % Weight | 4 | 5 | 6 |
| Chloridric acid | 2 | | |
| Linear C10 alkyl sulphate | 1.3 | 2 | 3 |
| n-Butoxy Propoxy Propanol | 2 | | 1.75 |
| Citric Acid | | 3 | 3 |
| PolyvinylPyrrolidone (Luviskol K60 ®) | 0.1 | 0.1 | 0.1 |
| NaOH | | 0.2 | 0.2 |
| Perfume | 0.4 | 0.4 | 0.4 |
| Polysaccharide (Xanthan Gum Kelzan T ®, Kelco) | 0.3 | 0.35 | 0.35 |
| Abrasive particles made from polyurethane foam: samples # 6 | 2 | 2 | 2 |
| Water | Balance | Balance | Balance |

| Hand-dishwashing detergent compositions: | | | |
|---|---|---|---|
| % Weight | 7 | 8 | 9 |
| N-2-ethylhexyl sulfocuccinamate | 3 | 3 | 3 |
| C11EO5 | 7 | 14 | |
| C11-EO7 | | | 7 |
| C10-EO7 | 7 | | 7 |
| Trisodium Citrate | 1 | 1 | 1 |
| Potassium Carbonate | 0.2 | 0.2 | 0.2 |
| Perfume | 1 | 1 | 1 |
| Polysaccharide (Xanthan Gum Kelzan T ®, Kelco) | 0.35 | 0.35 | 0.35 |
| Abrasive particles made from polyurethane foam: samples # 6 | 2 | 2 | 2 |
| Water (+minor e.g.; pH adjusted to 10.5) | Balance | Balance | Balance |

| General degreaser composition: | | |
|---|---|---|
| % Weight | 10 | 11 |
| C9-C11 EO8 (Neodol 91-8 ®) | 3 | 3 |
| N-Butoxy Propoxy Propanol | 15 | 15 |
| Ethanol | 10 | 5 |
| Isopropanol | | 10 |
| Polysaccharide (Xanthan Gum-glyoxal modified Optixan-T) | 0.35 | 0.35 |
| Abrasive particles made from polyurethane foam: samples # 1 | 1 | 1 |
| Water (+minor e.g.; pH adjusted to alkaline pH) | Balance | Balance |

| Scouring composition: | | | |
|---|---|---|---|
| % Weight | 12 | 13 | 14 |
| Sodium C13-16 prafin sulfonate | 2.5 | 2.5 | 2.5 |
| C12-14-EO7 (Lutensol AO7 ®) | 0.5 | 0.5 | 0.5 |
| Coconut Fatty Acid | 0.3 | 0.3 | 0.3 |
| Sodium Citrate | 3.3 | 3.3 | 3.3 |
| Sodium Carbonate | 3 | 3 | 3 |
| Orange terpenes | 2.1 | 2.1 | 2.1 |
| Benzyl Alcohol | 1.5 | 1.5 | |
| Polyacrylic acid 1.5Mw | 0.75 | 0.75 | 0.75 |
| Diatomaceous earth (Celite 499 ® median size 10 μm) | 25 | | |
| Calcium Carbonate (Merk 2066 ® median size 10 μm) | | 25 | |
| Abrasive particles made from polyurethane foam: samples # 1 | 5 | 5 | 5 |
| Water | Balance | Balance | Balance |

| Liquid glass cleaner: | | |
| --- | --- | --- |
| % Weight | 15 | 16 |
| Butoxypropanol | 2 | 4 |
| Ethanol | 3 | 6 |
| C12-14 sodium sulphate | 0.24 | |
| NaOH/Citric acid | To pH 10 | |
| Citric Acid | | |
| Abrasive particles made from polyurethane foam: samples # 1 (bis) | 0.5 | 0.5 |
| Water (+minor) | Balance | Balance |

| Cleaning wipe (Body cleansing wipe): | | | |
| --- | --- | --- | --- |
| % Weight | 17 | 18 | 19 |
| C10 Amine Oxide | — | 0.02 | — |
| C12,14 Amine Oxide | 0.4 | — | — |
| Betaine (Rewoteric AM CAS 15 U) | — | — | 0.2 |
| C9,11 A5EO (Neodol E 91.5 ®) | — | 0.1 | — |
| C9,11 A8EO (Neodol E 91.8 ®) | — | — | 0.8 |
| C12,14 A5EO | 0.125 | — | — |
| 2-Ethyl Hexyl Sulphate | — | 0.05 | 0.6 |
| Silicone | 0.001 | 0.003 | 0.003 |
| EtOH | 9.4 | 8.0 | 9.5 |
| Propylene Glycol Butyl Ether | 0.55 | 1.2 | — |
| Geraniol | — | — | 0.1 |
| Citric acid | 1.5 | — | — |
| Lactic acid | — | — | 1.5 |
| Perfume | 0.25 | 0.15 | 0.15 |
| Abrasive particles made from polyurethane foam: samples # 1 bis | 0.5 gram/sqm | 1 gram/sqm | 3 gram/sgm |
| Nonwoven: Spunlace 100% viscose 50 gsm (lotion loading fact) | | | (x3.5) |
| Nonwoven: Airlaid walkisoft (70% cellulose, 12% Viscose, 18% binder) 80 gsm (lotion loading factor) | | (x3.5) | |
| Carded thermobonded (70% polypropylene, 30% rayon), 70 gsm (Lotion loading factor) | (x3.5) | | |

| % Weight | 20 |
| --- | --- |
| Benzalkonioum Chloride (Alkaquat DMB-451 ®) | 0.1 |
| Cocamine Oxide (C10/C16 alkyl dimethyl amine oxide; AO-1214 LP supplied by Procter & Gamble Co.) | 0.5 |
| Pyroglutamic Acid (pidolidone) (2-pyrrolidone-5 carboxylic acid) | 4 |
| Ethanol-denatured 200 proof (SD alcohol 40 ®) | 10 |
| DC Antiform H-10 (dimethicone) | 0.03 |
| Sodium Benzoate | 0.2 |
| Tetrasodium EDTA (Hampene 220 ®) | 0.1 |
| Sodium Chloride | 0.4 |
| Perfume | 0.01 |
| Water and minors | balance |

The above wipes lotion composition is loaded onto a water-insoluble substrate, being a patterned hydroentangled nonwoven substrate having a basis weight of 56 grams per square meter comprising 70% polyester and 30% rayon approximately 6.5 inches wide by 7.5 inches long with a caliper of about 0.80 mm. Optionally, the substrate can be pre-coated with dimethicone (Dow Corning 200 Fluid 5cst) using conventional substrate coating techniques. Lotion to wipe weight ratio of about 2:1 using conventional substrate coating techniques. Abrasive particles made from polyurethane foam (samples # 1 bis) are loaded on the wipe e.g.: via the wipe lotion in way to achieve 0.2-3 gram particles/sqm substrate

| Oral care composition (toothpaste): | | |
| --- | --- | --- |
| % Weight | 20 | 21 |
| Sorbitol (70% sol.) | 24.2 | 24.2 |
| Glycerin | 7 | 7 |
| Carboxymethylcellulose | 0.5 | 0.5 |
| PEG-6 | 4 | 4 |
| Sodium Fluoride | 0.24 | 0.24 |
| Sodium Saccharine | 0.13 | 0.13 |
| Mono Sodium phosphate | 0.41 | 0.41 |
| Tri Sodium phosphate | 0.39 | 0.39 |
| Sodium Tartrate | 1 | 1 |
| TiO2 | 0.5 | 0.5 |
| Silica | 35 | |
| Sodium lauroyl sarcosinate (95% active) | 1 | 1 |
| Flavor | 0.8 | 0.8 |
| Abrasive particles made from polyurethane foam: samples # 1 (tris) | 2 | 5 |
| Water | Balance | Balance |

| Body Cleansing composition: | | |
| --- | --- | --- |
| % Weight | 22 | 23 |
| Cocoamidopropyl betaine | 5.15 | 5.15 |
| Sodium Laureth sulfate | 5.8 | 5.8 |
| Sodium Lauroyl sarcosinate | 0.5 | 0.5 |
| Polyquaternium 10 | 0.1 | 0.1 |
| C12-14 fatty alcohol | 0.45 | 0.45 |
| Zinc Stearate | 1.5 | 1.5 |
| Glycol DiStearate | 0.25 | 0.25 |
| Sodium lauryl sulfate | 0.53 | 0.53 |
| Cocamidopropyl betaine | 0.17 | 0.17 |
| Lauramide Diethanolamide | 0.48 | 0.48 |
| Sodium sulfate | 0.05 | 0.05 |
| Citric Acid | 0.05 | 0.05 |
| DMDM hydantoin (1,3-Dimethylol-5,5-dimethylhydantoin Glydant) | 0.2 | 0.2 |
| Tetra Sodium EDTA | 0.1 | 0.1 |
| Fragance | 0.5 | 0.5 |
| Polysaccharide (Xanthan Gum-glyoxal modified Optixan-T) | 0.2 | 0.2 |
| Abrasive particles made from polyurethane foam: samples # 12 | 2 | 1 |
| Water and minors | | 1 |
| Water | Balance | Balance |

| Facial Cleansing Compositions | | | | |
| --- | --- | --- | --- | --- |
| Ingredients | 24 | 25 | 26 | 27 |
| Acrylates Copolymer[1] | 1.50 | 2.0 | 1.25 | — |
| Acrylates/C$_{10-30}$ alkyl acrylate crosspolymer[2] | — | — | — | 1.0 |
| Sodium Lauryl Sulfate | 2.0 | — | — | — |

-continued

Facial Cleansing Compositions

| Ingredients | 24 | 25 | 26 | 27 |
|---|---|---|---|---|
| Sodium Laureth Sulfate | 8.0 | — | — | — |
| Ammonium Lauryl Sulfate | — | 6.0 | — | — |
| Sodium Trideceth Sulfate | — | — | 3.0 | 2.5 |
| Sodium Myristoyl Sarcosinate | — | 2.0 | 3.0 | 2.5 |
| Sodium Lauroamphoacetate[3] | — | — | 6.0 | 5.0 |
| Sodium Hydroxide* | pH > 6 | — | — | — |
| Triethanolamine* | — | pH > 6 | — | pH 5.2 |
| Cocamidopropyl Betaine | 4.0 | 7.0 | — | — |
| Glycerin | 4.0 | 5.0 | 2.0 | 2.0 |
| Sorbitol | — | — | 2.0 | 2.0 |
| Salicylic Acid | — | — | 2.0 | 2.0 |
| Fragrance | 0.1 | 0.1 | 0.1 | 0.1 |
| Preservative | 0.3 | 0.3 | 0.15 | 0.15 |
| Abrasive particles made from polyurethane foam: samples # 1 (bis) | 1.0 | 1.0 | 2.0 | 2.0 |
| PEG 120 Methyl Glucose Trioleate[4] | 0.5 | — | 0.25 | 0.25 |
| PEG 150 Pentaerythrityl Tetrastearate[5] | — | 0.40 | — | — |
| Citric Acid** | pH 5.5 | pH 5.5 | pH 5.5 | pH 5.5 |
| Water | QS to 100% | QS to 100% | QS to 100% | QS to 100% |

*per the supplier use directions, the base is used to activate the acrylates copolymer
**acid can be added to adjust the formula to a lower pH
[1]Carbopol Aqua SF-1 ® from Noveon ™, Inc.
[2]Carbopol Ultrez 21 ® from Noveon ™, Inc.
[3]Miranol ® Ultra L32 from Rhodia
[4]Glucamate LT ® from Chemron
[5]Crothix ® from Croda Examples 24 to 27 are made the following way:

Add Carbopol® to de-ionized free water of the formulation. Add all surfactants except cationics and betaines. If the pH is less than 6 then add a neutralizing agent (typically a base i.e., Triethanolamine, sodium hydroxide) to adjust to a pH greater than 6. If necessary, apply gentle heat to reduce viscosity and help minimize air entrapment. Add betaine and/or cationic surfactants. Add conditioning agents, additional rheology modifiers, pearlizing agents, encapsulated materials, exfoliants, preservatives, dyes, fragrances, abrasive particles and other desirable ingredients. Lastly, if desired reduce the pH with an acid (i.e. citric acid) and increase viscosity by adding sodium chloride.

Oral care composition (toothpaste)

| | 28 | 29 | 30 | 31 | 32 |
|---|---|---|---|---|---|
| Sodium Gluconate | 1.064 | 1.064 | 1.064 | 1.064 | 0.600 |
| Stannous fluoride | 0.454 | 0.454 | 0.454 | 0.454 | 0.454 |
| Sodium fluoride | — | — | — | — | — |
| Sodium monofluorophosphate | — | — | — | — | — |
| Zinc Lactate | 0.670 | 0.670 | 0.670 | 0.670 | 2.500 |
| Glycerin | — | — | — | — | 36.000 |
| Polyethylene glycol 300 | — | — | — | — | 7.000 |
| Propylene Glycol | — | — | — | — | 7.000 |
| Sorbitol(LRS) USP | 39.612 | 39.612 | 39.612 | 39.612 | — |
| Sodium lauryl sulfate solution (28%) | 5.000 | 5.000 | 5.000 | 5.000 | 3.500 |
| Abrasive particles made from polyurethane foam: samples # 1 (bis) | 10.000 | 10.000 | 1.000 | 5.000 | 5.000 |
| Zeodent 119 | — | — | — | — | — |
| Zeodent 109 | — | — | 10.000 | 10.000 | 10.000 |
| Hydrogen peroxide (35% soln) | — | — | — | — | — |
| Sodium hexametaphosphate | — | — | — | — | 13.000 |
| Gantrez | — | 2.000 | 2.000 | 2.000 | — |
| Natural CaCO3-600M | — | — | — | — | — |
| Sodium phosphate (mono basic) | — | — | — | — | — |
| Sodium phosphate (Tri basic) | — | — | — | — | 1.000 |
| Zeodent 165 | — | — | — | — | — |
| Cocoamidopropyl Betaine (30% Soln) | — | — | — | — | — |
| Cetyl Alcohol | 3.000 | — | — | — | — |
| Stearyl Alcohol | 3.000 | — | — | — | — |
| Hydroxyethyl cellulose (HEC Natrasol 250M) | — | 0.500 | 0.500 | 0.500 | — |
| CMC 7M8SF | — | 1.300 | 1.300 | 1.300 | — |
| Xanthan Gum | — | — | — | — | 0.250 |
| Poloxamer 407 | — | — | — | — | — |
| Carrageenan mixture | — | 0.700 | 0.700 | 0.700 | 0.600 |
| Titanium dioxide | — | — | — | — | — |
| Saccharin Sodium | 0.500 | 0.500 | 0.500 | 0.500 | 0.500 |
| Flavor | 1.000 | 1.000 | 1.000 | 1.000 | 1.000 |
| Water | QS | QS | QS | QS | QS |

Zeodent 119, 109 and 165 are precipitated silica materials sold by the J. M. Huber Corporation.

Gantrez is a copolymer of maleic anhydride or acid and methyl vinyl ether.

CMC 7M8SF is a sodium carboxymethylcellulose.

Poloxamer is a difunctional block-polymer terminating in primary hydroxyl groups.

|  | 33 | 34 | 35 | 36 | 37 |
|---|---|---|---|---|---|
| Sodium Gluconate | — | — | — | — | — |
| Stannous fluoride | — | — | — | — | — |
| Sodium fluoride | — | 0.243 | 0.243 | 0.243 | — |
| Sodium monofluorophosphate | 1.10 | — | — | — | — |
| Zinc Lactate | — | — | — | — | — |
| Glycerin | — | — | — | — | 40.000 |
| Polyethylene glycol 300 | — | — | — | — | — |
| Propylene Glycol | | | | | |
| Sorbitol(LRS) USP | 24.000 | 42.500 | 42.500 | 42.500 | 30.000 |
| Sodium lauryl sulfate solution (28%) | 4.000 | 4.000 | — | 4.000 | — |
| Abrasive particles made from polyurethane foam: samples # 1 (bis) | 5.000 | 10.000 | 10.000 | 5.000 | 15.000 |
| Zeodent 119 | — | — | — | 10.000 | — |
| Zeodent 109 | | | | | |
| Hydrogen peroxide (35% soln) | — | — | — | — | — |
| Sodium hexametaphosphate | — | — | — | — | — |
| Gantrez | | | | | |
| Natural CaCO3-600M | 35.00 | — | — | — | — |
| Sodium phosphate (mono basic) | 0.10 | 0.420 | 0.420 | 0.420 | 0.420 |
| Sodium phosphate (Tri basic) | 0.40 | 1.100 | 1.100 | 1.100 | 1.100 |
| Zeodent 165 | 2.00 | — | — | — | 2.000 |
| Cocoamidopropyl Betaine (30% Soln) | — | — | 5.000 | — | — |
| Cetyl Alcohol | 0.000 | — | — | — | — |
| Stearyl Alcohol | 0.000 | — | — | — | — |
| Hydroxyethyl cellulose (HEC Natrasol 250M) | — | 0.500 | 0.500 | 0.500 | — |
| CMC 7M8SF | 1.300 | 1.300 | 1.300 | 1.300 | 1.300 |
| Xanthan Gum | — | — | — | — | — |
| Poloxamer 407 | — | — | — | — | — |
| Carrageenan mixture | — | 0.700 | 0.700 | 0.700 | — |
| Titanium dioxide | — | — | — | — | — |
| Saccharin Sodium | 0.250 | 0.500 | 0.500 | 0.500 | 0.500 |
| Flavor | 1.000 | 1.000 | 1.000 | 1.000 | 1.000 |
| Water | QS | QS | QS | QS | QS |

|  | 38 | 39 | 40 |
|---|---|---|---|
| Sodium Gluconate | — | — | 1.500 |
| Stannous fluoride | — | — | 0.454 |
| Sodium fluoride | — | — | — |
| Sodium monofluorophosphate | — | — | — |
| Zinc Lactate | — | — | — |
| Glycerin | 40.000 | 10.000 | 25.000 |
| Polyethylene glycol 300 | 3.000 | — | — |
| Propylene Glycol | — | — | — |
| Sorbitol(LRS) USP | — | 39.612 | — |
| Sodium lauryl sulfate solution (28%) | 5.000 | 4.000 | 4.000 |
| Abrasive particles made from polyurethane foam: samples # 1 (bis) | 15.000 | 5.000 | 5.000 |
| Zeodent 119 | — | — | — |
| Zeodent 109 | | | |
| Hydrogen peroxide (35% soln) | — | 8.570 | 8.570 |
| Sodium hexametaphosphate | 14.000 | — | — |
| Gantrez | — | — | — |
| Natural CaCO3-600M | — | — | — |
| Sodium phosphate (mono basic) | 0.420 | — | — |
| Sodium phosphate (Tri basic) | 1.100 | — | — |
| Zeodent 165 | 2.000 | — | — |
| Cocoamidopropyl Betaine (30% Soln) | — | — | — |
| Cetyl Alcohol | — | 3.000 | — |
| Stearyl Alcohol | — | 3.000 | — |
| Hydroxyethyl cellulose (HEC Natrasol 250M) | — | — | — |
| CMC 7M8SF | 1.000 | — | — |
| Xanthan Gum | 0.300 | — | — |
| Poloxamer 407 | 0.500 | — | 18.000 |
| Carrageenan mixture | — | — | — |
| Titanium dioxide | 0.500 | — | — |
| Saccharin Sodium | 0.500 | 0.500 | 0.500 |
| Flavor | 1.000 | 1.000 | 1.000 |
| Water | QS | QS | QS |

Hair Shampoo

|  | 41 | 42 | 43 |
|---|---|---|---|
| Water | q.s. | q.s. | q.s. |
| Polyquaterium 76[1] | 0.25 | — | — |
| Guar, Hydroxylpropyl Trimonium Chloride[2] | — | 0.25 | — |
| Polyquaterium 6[3] | — | — | 0.25 |
| Sodium Laureth Sulfate | 12 | 10.5 | 10.5 |
| Sodium Lauryl Sulfate | — | 1.5 | 1.5 |
| Silicone[4] | 0.75 | 1.00 | 0.5 |
| Cocoamidopropyl Betaine | 3.33 | 3.33 | 3.33 |
| Cocoamide MEA | 1.0 | 1.0 | 1.0 |
| Ethylene Glycol Distearate | 1.50 | 1.50 | 1.50 |
| Abrasive particles made from polyurethane foam: samples # 1 (bis) | 1 | — | 2 |
| Crosslinked PS-DVB (50% DVB 55, mean diameter D(v, 0.9) 75 μm) abrasive cleaning particles | — | 1 | — |
| Fragrance | 0.70 | 0.70 | 0.70 |
| Preservatives, pH & Visc. adjusters | Up to 1% | Up to 1% | Up to 1% |

[1]Copolymer of Acrylamide(AM) and TRIQUAT, MW = 1,000,000; CD = 1.6 meq./gram; Rhodia
[2]Jaguar C500, MW - 500,000, CD = 0.7, Rhodia
[3]Mirapol 100S, 31.5% active, Rhodia
[4]Dimethicone Fluid, Viscasil 330M; 30 micron particle size; Momentive Silicones The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid cleaning and/or cleansing composition comprising from about 1.0% to about 3% by weight of the composition of particles as abrasive cleaning particles and from about 65% to about 99.5% by weight of the composition of water, wherein said abrasive cleaning particles have been reduced from a foam via grinding or milling, and wherein said foam has a density from about 5 kg/m³ to about 150 kg/m³, and wherein said foam has a cell size from about 40 micrometers to about 700 micrometers, wherein the particles have a mean circularity of from about 0.1 to about 0.4, a mean solidity of from about 0.4 to about 0.75 and a mean roughness of from about 0.1 to about 0.3, wherein the abrasive cleaning particles are colored polyurethane, wherein the colored polyurethane cleaning particles are color stable.

2. A liquid cleaning and/or cleansing composition according to claim 1, wherein said foam has density preferably from about 20 kg/m$^3$ to about 90 kg/m$^3$.

3. A liquid cleaning and/or cleansing composition according to claim 2, wherein said foam has cell size preferably from about 100 micrometers to about 500 micrometers.

4. A liquid cleaning and/or cleansing composition according to claim 3, wherein said foam has preferably less than about less than 30% of the cells closed.

5. A liquid cleaning and/or cleansing composition according to claim 4, wherein said abrasive cleaning particles have a strut value from about 1.5 to about 10.

6. A liquid cleaning and/or cleansing composition according to claim, 5 wherein said abrasive cleaning particles population contains an amount of particles with size below half of the average foam cell size below about 30% by weight whereas the particle size weight proportion is defined by physical sieving method.

7. A liquid cleaning and/or cleansing composition according to claim 1, wherein said abrasive cleaning particles have HV Vickers hardness from about 3 to about 50 kg/mm$^2$.

8. A liquid cleaning and/or cleansing composition according to claim 7, wherein said abrasive particles have a mean particle size as expressed by the area-equivalent diameter from about 10 to about 1000 µm according to ISO 9276-6.

9. A liquid cleaning and/or cleansing composition according to claim 8, wherein said abrasive has sharp edges, said edges having a tip radius below about 20 µm.

10. A liquid cleaning and/or cleansing composition according to claim 9, further comprises a suspending aid, wherein said suspending aid is selected from the group consisting of polycarboxylate polymer thickeners; hydroxyl-containing fatty acid, fatty ester materials; carboxymethylcellulose, ethyl cellulose, hydroxyethyl cellulose, hydroxypropyl cellulose, hydroxymethyl cellulose, succinoglycan and naturally occurring polysaccharide polymers, or mixtures thereof.

11. A liquid cleaning and/or cleansing composition according to claim 1, whereas the cleaning composition is loaded on a cleaning substrate whereas the substrate is a paper or nonvowen towel or wipe or a sponge.

12. A process of cleaning and/or cleansing a surface with a liquid, cleaning and/or cleansing composition according to claim 1, wherein said surface is contacted with said composition, and wherein said composition is applied onto said surface.

13. A process according to claim 12, wherein said surface is an inanimate surface, selected from the group consisting of household hard surfaces; dish surfaces; leather; synthetic leather; and automotive vehicles surfaces.

14. A process according to claim 12, wherein said surface is an animate surface, selected from the group consisting of: human skin; animal skin; human hair; animal hair; and hard and soft tissue surface of the oral cavity.

* * * * *